United States Patent
Yamashita et al.

(10) Patent No.: US 9,764,063 B2
(45) Date of Patent: Sep. 19, 2017

(54) METHOD FOR PRODUCING MIXED CELL POPULATION OF CARDIOMYOCYTES AND VASCULAR CELLS FROM INDUCED PLURIPOTENT STEM CELL

(71) Applicant: IHEART JAPAN CORPORATION, Kyoto-shi, Kyoto (JP)

(72) Inventors: Jun Yamashita, Kyoto (JP); Hidetoshi Masumoto, Kyoto (JP)

(73) Assignee: IHEART JAPAN CORPORATION, Kyoto-shi (JP)

(*) Notice: Subject to any disclaimer, the term of this patent is extended or adjusted under 35 U.S.C. 154(b) by 152 days.

(21) Appl. No.: 14/385,086

(22) PCT Filed: Mar. 15, 2013

(86) PCT No.: PCT/JP2013/058460
§ 371 (c)(1),
(2) Date: Sep. 12, 2014

(87) PCT Pub. No.: WO2013/137491
PCT Pub. Date: Sep. 19, 2013

(65) Prior Publication Data
US 2015/0297794 A1   Oct. 22, 2015

Related U.S. Application Data

(60) Provisional application No. 61/611,340, filed on Mar. 15, 2012.

(51) Int. Cl.
| | |
|---|---|
| A61L 27/38 | (2006.01) |
| A61L 27/50 | (2006.01) |
| C12N 5/071 | (2010.01) |
| A61L 27/54 | (2006.01) |
| A61K 35/34 | (2015.01) |
| A61K 35/44 | (2015.01) |
| A61K 35/545 | (2015.01) |
| C12N 5/077 | (2010.01) |

(52) U.S. Cl.
CPC .......... *A61L 27/3886* (2013.01); *A61K 35/34* (2013.01); *A61K 35/44* (2013.01); *A61K 35/545* (2013.01); *A61L 27/3808* (2013.01); *A61L 27/3826* (2013.01); *A61L 27/3834* (2013.01); *A61L 27/3839* (2013.01); *A61L 27/3895* (2013.01); *A61L 27/50* (2013.01); *A61L 27/54* (2013.01); *C12N 5/0602* (2013.01); *C12N 5/069* (2013.01); *C12N 5/0657* (2013.01); *C12N 5/0697* (2013.01); *A61L 27/3804* (2013.01); *A61L 2300/608* (2013.01); *A61L 2300/64* (2013.01); *A61L 2430/20* (2013.01); *C12N 2500/44* (2013.01); *C12N 2501/115* (2013.01); *C12N 2501/16* (2013.01); *C12N 2501/165* (2013.01); *C12N 2501/727* (2013.01); *C12N 2502/1329* (2013.01); *C12N 2502/28* (2013.01); *C12N 2506/45* (2013.01); *C12N 2539/10* (2013.01)

(58) Field of Classification Search
None
See application file for complete search history.

(56) References Cited

U.S. PATENT DOCUMENTS

| | | | |
|---|---|---|---|
| 2004/0009566 A1 | 1/2004 | Okano et al. | |
| 2009/0269314 A1* | 10/2009 | Keller | C12N 5/0657 424/93.7 |

FOREIGN PATENT DOCUMENTS

| | | |
|---|---|---|
| EP | 1 674 562 A1 | 6/2006 |
| EP | 2692859 A1 | 2/2014 |
| JP | 2007-528755 A | 10/2007 |
| JP | 2012-210156 A | 11/2012 |
| WO | WO 02/08387 A1 | 1/2002 |
| WO | WO 2005/011524 A1 | 2/2005 |

OTHER PUBLICATIONS

Masuda, Shinako; et al; "Cell sheet engineering for heart tissue repair" Advanced Drug Delivery Reviews, 60, 277-285, 2008.*
Gaengel, Konstantin; et al; "Endothelial-Mural Cell Signaling in Vascular Development and Angiogenesis" Arteriosclerosis, Thrombosis, and Vascular Biology, 29, 630-638, 2009.*
Caspi, Oren; et al; "Tissue Engineering of Vascularized Cardiac Muscle From Human Embryonic Stem Cells" Circulation Research, 100, 263-272, 2007.*
Schopperle, William M; DeWolf, William C; "The TRA-1-60 and TRA-1-81 Human Pluripotent Stem Cell Markers Are Expressed on Podocalyxin in Embryonal Carcinoma" Stem Cells, 25, 723-730, 2007.*
Bel et al. "Composite Cell Sheets: A Further Step Toward Safe and Effective Myocardial Regeneration by Cardiac Progenitors Derived From Embryonic Stem Cells", Circulation, 2010, 122: S118-S123.
International Search Report, issued in PCT/JP2013/058460, dated Apr. 23, 2013.
Jun Yamashita "Myocardial Regeneration Using iPS Cells", Shinzo, 43 (1), 2011, pp. 4-9.
Jun Yamashita "Studies regarding Induction of Differentiation of Human Induced Pluripotent Stem (iPS) Cell-Derived Cardiac Cells and Application Thereof for Medical Transplantation", 2011, pp. 1-6.
Laflamme et al. "Heart regeneration", Nature, 473, 2011, pp. 326-335.

(Continued)

*Primary Examiner* — David Berke-Schlessel
(74) *Attorney, Agent, or Firm* — Birch, Stewart, Kolasch & Birch, LLP

(57) ABSTRACT

The present invention provides: a method for producing mixed cells comprising cardiomyocytes, endothelial cells and mural cells from induced pluripotent stem cells, the method comprising (a) a step of producing cardiomyocytes from induced pluripotent stem cells and (b) a step of culturing the cardiomyocytes in the presence of VEGF; and a therapeutic agent for heart diseases, comprising the mixed cells produced by the method.

12 Claims, 10 Drawing Sheets
(4 of 10 Drawing Sheet(s) Filed in Color)

(56) References Cited

OTHER PUBLICATIONS

Masumoto et al. "Transplantation of Cell Sheets with Human iPS Cell-derived Cardiomyocytes and Vascular Cells for Infarcted Hearts: A Basic Study", Circulation, 126 (21 suppl.), 2012, abstract No. A11848.

Narazaki et al. "Directed and Systematic Differentiation of Cardiovascular Cells From Mouse Induced Pluripotent Stem Cells", Circulation, 2008, 118, pp. 498-506.

Sekine et al. "Cardiomyocyte Sheets Co-Cultured With Endothelial Cells Improve Cardiac Function of Ischemic Heart", Japan Research Promotion Society for Cardiovascular Disease Heisei 18 Nendo Kenkyu Gyosekishu, 2006, (21), pp. 5-8.

Sekine et al. "Transplantation of Cardiomyocyte Sheets Co-Cultured With Endothelial Cells for Ischemic Heart Failure", Dai 19 Kai Japanese Association of Cardiovascular Pharmacology Koen Yoshishu, 2009, pp. 34.

Shimizu et al. "Cell sheet engineering for myocardial tissue reconstruction", Biomaterials 24, 2003, 2309-2316.

Shimizu et al. "Polysurgery of cell sheet grafts overcomes diffusion limits to produce thick, vascularized myocardial tissues", The FASEB Journal 20: 708-10, 2006.

Uosaki et al. "Efficient and Scalable Purification of Cardiomyocytes from Human Embryonic and Induced Pluripotent Stem Cells by VCAM1 Surface Expression", PLoS One, 2011, 6 (8), e23657.

Written Opinion of the International Searching Authority, issued in PCT/JP2013/058460, dated Apr. 23, 2013.

Yang et al. "Human cardiovascular progenitor cells develop from a KDR+ embryonic-stem-cell-derived population", Nature, 453, 2008, pp. 524-528.

Extended European Search Report issued Jul. 24, 2015, in European Patent Application No. 13760866.7.

Kattman et al., "Multipotent Flk-1+Cardiovascular Progenitor Cells Give Rise to the Cardiomyocyte, Endothelial and Vascular Smooth Muscle Lineages," Developmental cell (Nov. 2006), vol. 11, pp. 723-732.

Matsuura et al., "Cell sheet-based cardiac tissue engineering using IPS cells," Medical Development (Dec. 31, 2011), vol. 239, No. 14, pp. 1352-1356, with partial English translation.

Notice of Reasons of Rejection issued Dec. 15, 2015, in Japanese Patent Application No. 2014-505050, with partial English translation.

Taura et al., "Induction and Isolation of Vascular Cells from Human Induced Pluripotent Stem Cells—Brief Report," Arterioscler. Thromb. Vasc. Biol. (2009), vol. 29, pp. 1100-1103.

Taura, D., "Induction and isolation of vascular cells from human induced pluripotent stem cells," Kyoto University Research Information Repository (Jan. 25, 2010) (URL: http://hdl.handle.net/2433/97941).

* cited by examiner

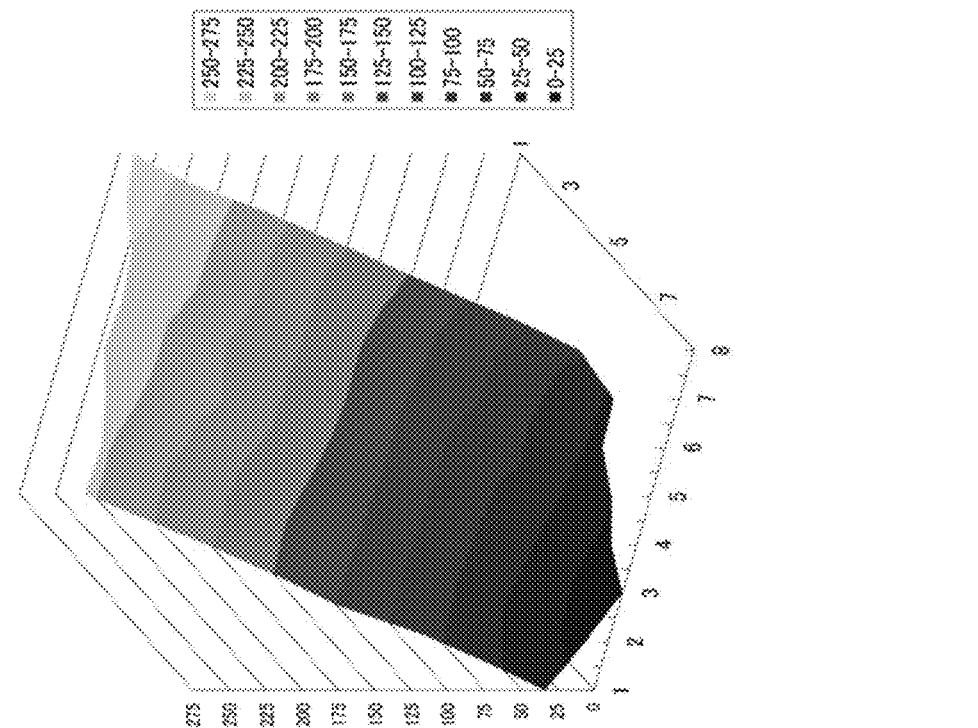
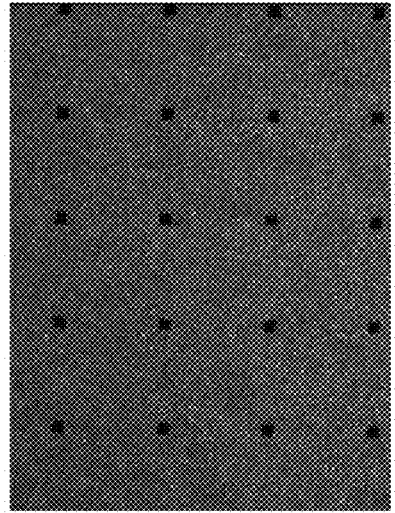
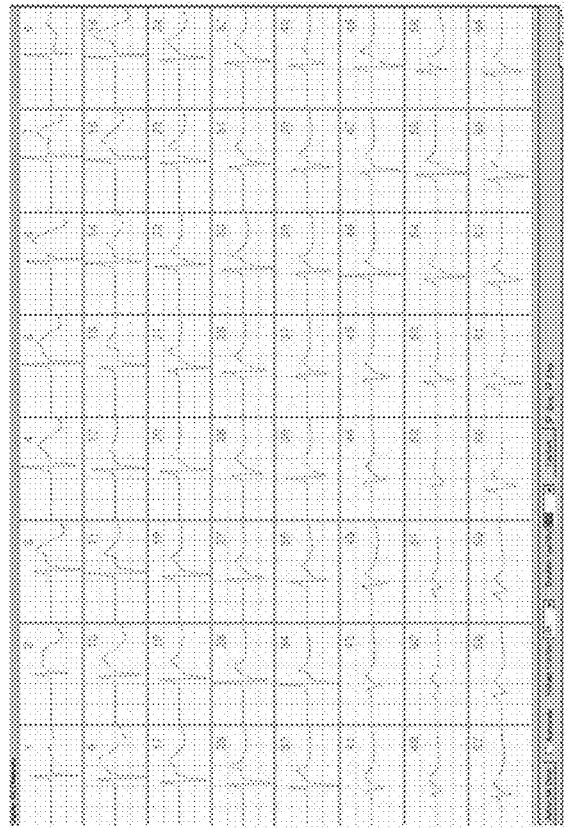
Fig. 3

Fig. 4
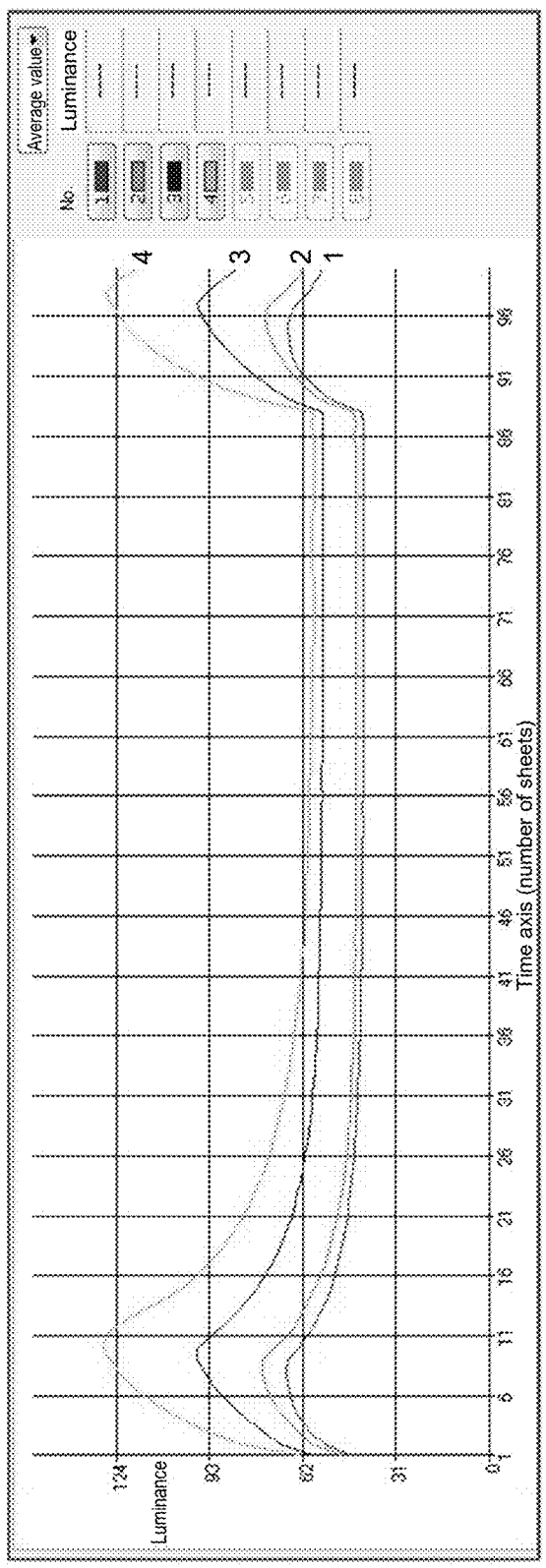
A
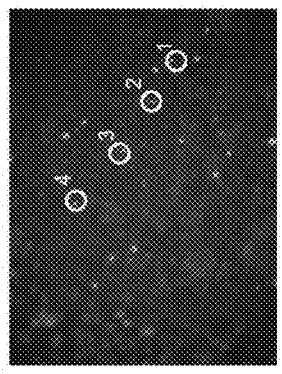
B

Fig. 6
A
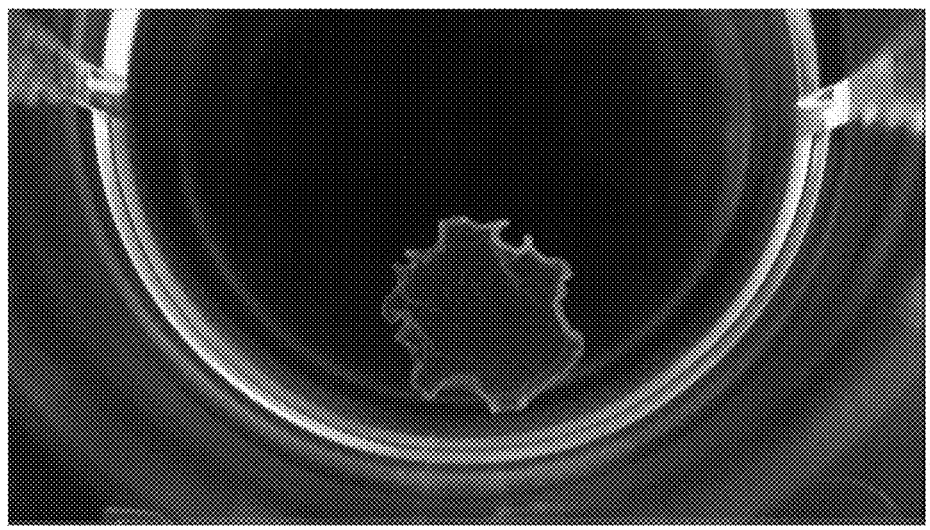
B
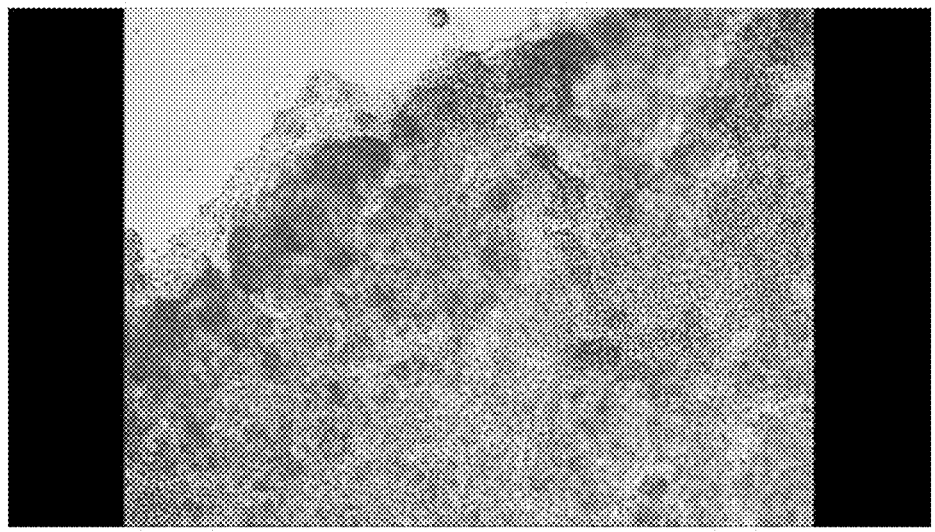

Fig. 8
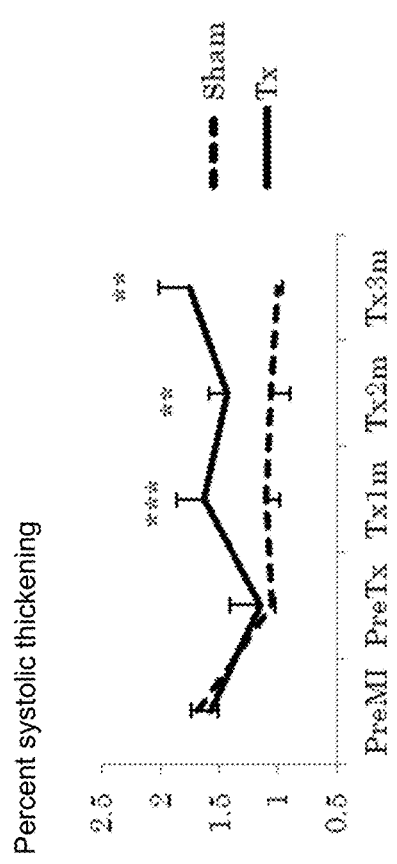
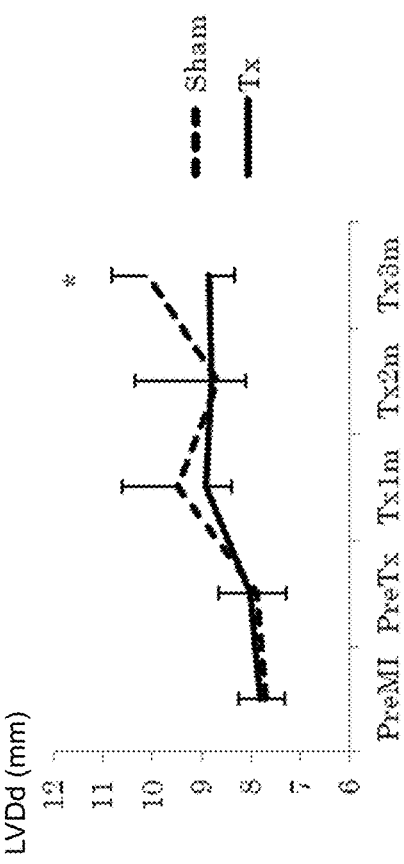
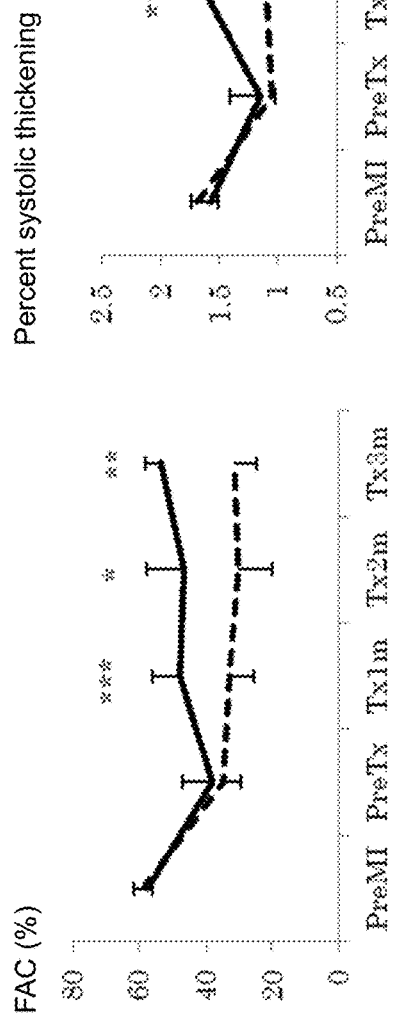
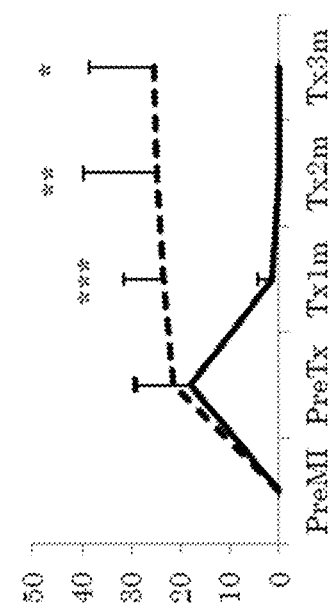

METHOD FOR PRODUCING MIXED CELL POPULATION OF CARDIOMYOCYTES AND VASCULAR CELLS FROM INDUCED PLURIPOTENT STEM CELL

CROSS REFERENCE TO RELATED APPLICATIONS

This application is the National Phase of PCT/JP2013/058460 filed on Mar. 15, 2013, which claims priority under 35 U.S.C. 119(e) to U.S. Provisional Application No. 61/611,340 filed on Mar. 15, 2012, all of which are hereby expressly incorporated by reference into the present application.

TECHNICAL FIELD

The present invention relates to a method for producing a mixed cell population of cardiomyocytes and vascular cells using induced pluripotent stem cells. The present invention also relates to a therapeutic agent for heart diseases, comprising the mixed cell population of cardiomyocytes and vascular cells obtained by the method.

BACKGROUND ART

Because cardiomyocytes in adults hardly proliferate, the loss of cardiomyocytes due to ischemic heart disease or the like results in irreversible damage. Currently, no drug or procedure clinically used exhibits efficacy in replacing a cardiac scar with a functional contractile tissue. Accordingly, a new therapy is desired for regenerating normal cardiomyocytes, and a replacement therapy has been proposed, which involves administering cardiomyocytes separately produced. In such a replacement therapy, it has been studied to administer the cardiomyocytes in a sheet form to engraft the cells in the heart of a recipient (Non Patent Literature 1 and Patent Literature 1). In addition, since the amount of the cells in the sheet is insufficient and thus expected therapeutic effect is not obtained, it is considered necessary to layer the sheet before administration (Non Patent Literature 2).

Methods are exemplified, which use fetal cardiomyocytes, myoblast cells, cardiac myoblasts derived from adipose tissue-derived stem cells, and cardiomyocytes derived from embryonic stem cells as sources for cardiomyocytes for sheet preparation (Patent Literature 2, Non Patent Literature 3, and Patent Literature 3 (Japanese Patent Application No. 2011-076235)).

However, it is not reported that the effect of administration of a myocardial sheet formed using differentiated cells derived from induced pluripotent stem cells (iPS cells) improved cardiac function.

CITATION LIST

Patent Literature

Patent Literature 1: International Publication No. WO2002/008387
Patent Literature 2: JP Patent Publication (Kohyo) No. 2007-528755
Patent Literature 3: JP Patent Publication (Kokai) No. 2012-210156

Non Patent Literature

Non Patent Literature 1: Shimizu, T, et al, Biomaterials 24, 2309-2316, 2003

Non Patent Literature 2: Shimizu T, et al. FASEB J. 20: 708-10, 2006
Non Patent Literature 3: Bel A, et al. Circulation 122: S118-23, 2010

SUMMARY OF INVENTION

The purpose of the present invention relates to a method for producing a firm myocardial sheet comprising cardiomyocytes as well as endothelial cells and mural cells derived from induced pluripotent stem cells, and a therapeutic agent for heart diseases, comprising the myocardial sheet obtained thereby. Thus, an object of the present invention is to provide a myocardial sheet prepared from mixed cells obtained by simultaneous differentiation induction of cardiomyocytes, endothelial cells, and mural cells from induced pluripotent stem cells.

As a result of intensive studies for solving the above-described problems, the present inventors have found that a myocardial sheet comprising cardiomyocytes, endothelial cells, and mural cells at a specified ratio is obtained by culturing induced pluripotent stem cells under culture conditions containing a particular factor. In addition, it has been found that cardiac function can be improved by implanting this sheet. The present invention has been accomplished based on these findings.

Thus, the present invention provides:
[1] a method for producing mixed cells composed of cardiomyocytes, endothelial cells, and mural cells from induced pluripotent stem cells, comprising the steps of:
(a) producing cardiomyocytes from induced pluripotent stem cells, and
(b) culturing the cardiomyocytes in the presence of VEGF (vascular endothelial growth factor);
[2] the method according to [1], wherein the VEGF has a concentration of 50 ng/mL to 100 ng/mL (both inclusive);
[3] the method according to [1] or [2], wherein the mixed cells have a endothelial cell content of 3% or more;
[4] the method according to any one of [1] to [3], wherein the step (a) is performed for 2 to 15 days and the step (b) is performed for 5 to 15 days;
[5] the method according to [4], wherein the step (a) is performed for 5 days and the step (b) is performed for 10 days;
[6] the method according to any one of [1] to [3], wherein the step (a) comprises the steps of:
(i) culturing induced pluripotent stem cells in a medium comprising Activin A, and
(ii) after the step (i), further performing culture in a medium comprising BMP4 (bone morphogenetic protein 4) and bFGF (basic fibroblast growth factor);
[7] the method according to [6], wherein the step (i) is performed for 1 to 5 days and the step (ii) is performed for 1 to 10 days;
[8] the method according to [7], wherein the step (i) is performed for 1 day and the step (ii) is performed for 4 days;
[9] the method according to any one of [1] to [8], further comprising a step of selecting TRA-1-60-negative cells from the cells obtained in the step (b);
[10] a therapeutic agent for heart diseases comprising the mixed cells obtained by the method according to any one of [1] to [9];
[11] a method for producing a myocardial sheet comprising a step of culturing the mixed cells produced by the method according to any one of [1] to [9] using a culture tool coated with a temperature-responsive polymer;

[12] the method according to [11], further comprising a step of layering the sheet;
[13] the method according to [12], wherein the layering forms 3 layers;
[14] the method according to [11], wherein the step is a step of culturing the mixed cells in a medium comprising serum;
[15] the method according to any one of [1] to [9] and [11] to [14], wherein the mixed cells are human cells;
[16] the therapeutic agent for heart diseases according to [10], wherein the mixed cells are human cells; and
[17] a therapeutic agent for heart diseases comprising the myocardial sheet obtained by the method according to any one of [11] to [15].

According to the method of the present invention, a myocardial sheet comprising cardiomyocytes, endothelial cells, and mural cells at a specified ratio can be produced from induced pluripotent stem cells. Using the myocardial sheet obtained, heart diseases can be treated, such as heart failure, ischemic heart disease, myocardial infarction, myocardiopathy, myocarditis, hypertrophic cardiomyopathy, dilated phase of hypertrophic cardiomyopathy, and dilated cardiomyopathy. In addition, the myocardial sheet obtained by the method according to the present invention can be used as a cardiac cell/tissue model for drug safety testing and drug discovery screening.

The present specification encompasses the contents of the specification and/or drawings of U.S. provisional application No. 61/611,340 on which the priority of the present application is based.

BRIEF DESCRIPTION OF DRAWINGS

The patent or application file contains at least one color drawing. Copies of this patent or patent application publication with color drawing will be provided by the USPTO upon request and payment of the necessary fee.

FIG. 3A is a drawing showing a sheet image adhering to MED64 probe. FIG. 3B is a drawing showing an extracellular potential at each electrode. FIG. 3C is a diagram schematically showing the distribution of the potentials measured in FIG. 3B. The electrode having the highest peak negative potential (the bottom of the figure) was set to a zero point, and color-coding was performed using the time difference (seconds) therefrom to the peak negative potential of each electrode. Conduction from the bottom toward the top is observed.

FIG. 4 is a graph showing the results of changes in the calcium concentration based on the detection of green fluorescence using Fluo8 (Nacalai Tesque) as an indicator (A and B). The fluorescence detection was carried out using BZ-9000 (Keyence).

FIG. 6A is a photograph showing a macroscopic finding of a layered sheet.

FIG. 6B is a photograph showing the optical microscope image of the layered sheet.

FIG. 8 is a series of graphs showing the results of cardiac ultrasonography up to 3 months after implantation. A and B are graphs showing changes in the left ventricular fractional area change (FAC) and the percent systolic thickening (both of which are indexes of left ventricular systolic performance) with time, respectively. C is a graph showing a change in the akinetic lesion (AL) (an index of the infarction range) with time. D is a graph showing a change in left ventricular diameter during diastole (an index of left ventricular dilatation). In the figure, PreMI indicates before myocardial infarction; PreTx, before treatment; Tx1m, 1 month after treatment; Tx2m, 2 months after treatment; and Tx3m, 3 months after treatment. * $p<0.05$,  $p<0.01$, * $p<0.001$ vs Sham.

DESCRIPTION OF EMBODIMENTS

Figure 1:
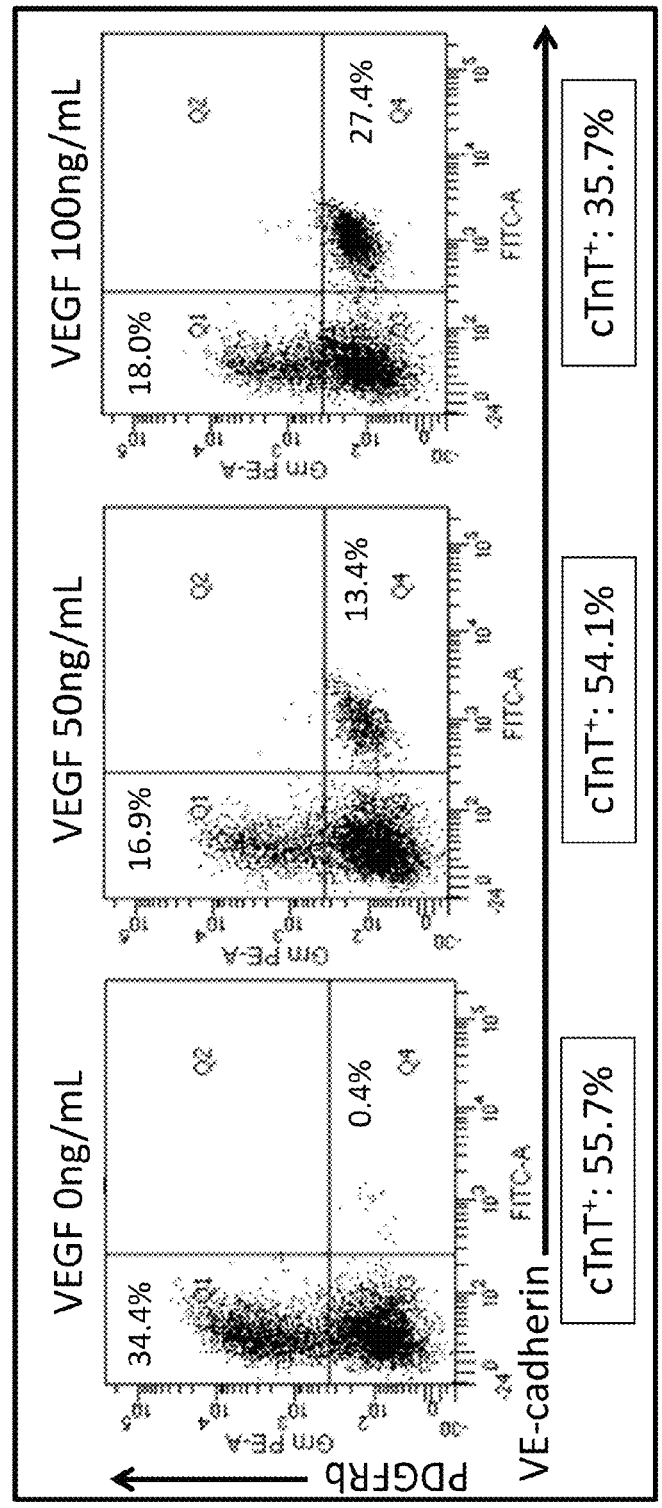
FIG. 1 is a set of graphs showing the cellular composition ratio of cardiomyocytes, endothelial cells, and mural cells simultaneously differentiation-induced by culture in the presence of VEGF in the late stage of differentiation induction from human iPS cells. In the figure, cTnT+, VE-cadherin, and PDGFRb indicate markers of cardiomyocytes, endothelial cells, and mural cells, respectively.

The present invention will be described below in detail.
As described above, the present invention relates to a method for producing a myocardial sheet from induced pluripotent stem cells, comprising (a) a step of producing cardiomyocytes, endothelial cells, and mural cells from induced pluripotent stem cells and (b) a step of forming a sheet using the cardiomyocytes, endothelial cells, and mural cells, and a therapeutic agent for heart diseases, comprising the myocardial sheet obtained by the method.

<Method for Producing Induced Pluripotent Stem Cell>

According to the present invention, the induced pluripotent stem (iPS) cells are somatic cell-derived artificial stem cells having almost the same characteristics, such as pluripotent differentiation and proliferative ability by self-renewal, as those of ES cells, which can be produced by introducing a particular nuclear reprogramming substance in the form of DNA or protein into somatic cells or increasing the endogenous expression of mRNA for, and a protein as, the nuclear reprogramming substance using an agent (K. Takahashi and S. Yamanaka (2006) Cell, 126: 663-676; K. Takahashi et al. (2007) Cell, 131: 861-872; J. Yu et al. (2007) Science, 318: 1917-1920; M. Nakagawa et al. (2008) Nat. Biotechnol., 26: 101-106; International Publication No. WO2007/069666; and International Publication No. WO2010/068955). The nuclear reprogramming substance is not particularly limited provided that it is a gene specifically expressed in ES cells or a gene playing an important role in maintaining the undifferentiation of ES cells, or a gene product thereof; examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb, Esrrg, and Glis1. These nuclear reprogramming substances may be used in combination in establishing iPS cells. For example, the nuclear reprogramming substances are used in combination including at least 1, or 2 or 3, preferably 4, thereof.

The information of the nucleotide sequences of mouse and human cDNAs of each of the nuclear reprogramming substances and the amino acid sequences of proteins encoded by the cDNAs can be obtained by referring to the NCBI accession numbers described in WO2007/069666, and the information of the mouse and human cDNA sequences and amino acid sequences of L-Myc, Lin28, Lin28b, Esrrb, Esrrg, and Glis1 can be obtained by referring to the following NCBI accession numbers. Those skilled in this art can prepare desired nuclear reprogramming substances by ordinary methods based on the cDNA or amino acid sequence information.

| Gene Name | Mouse | Human |
| --- | --- | --- |
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |

These nuclear reprogramming substances may be each introduced in the form of a protein into somatic cells by a technique, such as lipofection, binding to a cell-permeable peptide or microinjection, or can be introduced in the form of DNA into somatic cells by a technique, such as a vector (e.g., virus, plasmid, or artificial chromosome vector), lipofection, liposome, or microinjection. Examples of the virus vector include retroviral vectors, lentivirus vectors (both are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors, and Sendai virus vectors (Proc. Jpn Acad. Ser. B. Phys. Biol. Sci. 85, 348-62, 2009). Examples of the artificial chromosome vector include human artificial chromosomes (HAC), yeast artificial chromosomes (YAC), and bacterial artificial chromosomes (BAC, PAC). As the plasmid, a plasmid for mammalian cells can be used (Science, 322: 949-953, 2008). The vector can contain control sequences such as a promoter, an enhancer, a ribosomal binding site, a terminator, and a polyadenylation site in such a manner that the nuclear reprogramming substance can be expressed. Examples of the promoter to be used include EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR, and HSV-TK (herpes simplex virus thymidine kinase) promoter. Among others, EF1α promoter, CAG promoter, MoMuLV LTR, CMV promoter, and SRα promoter are exemplified. In addition, the vector may contain a selection marker sequence such as a drug resistance gene (e.g., a kanamycin-resistant gene, an ampicillin-resistant gene, or a puromycin-resistant gene), a thymidine kinase gene, or a diphtheria toxin gene, a reporter gene sequence such as a green fluorescence protein (GFP), β-glucuronidase (GUS), or FLAG, and the like, if necessary. In order to remove a gene encoding a nuclear reprogramming substance or both of a promoter and the gene encoding a nuclear reprogramming substance binding thereto after introduction into somatic cells, the vector may also have a LoxP sequence thereacross. In another preferable embodiment, after incorporating a transgene in a chromosome using a transposon, a method can be used which involves completely removing the transgene from the chromosome by causing a transferase to act on the cells using a plasmid vector or an adenovirus vector. Preferred examples of the transposon include piggyBac as a transposon derived from lepidopteran insects (Kaji, K. et al., (2009), Nature, 458: 771-775, Woltjen et al., (2009), Nature, 458: 766-770, and WO 2010/012077). Furthermore, the vector may contain the origin of lymphotrophic herpes virus, BK virus, or Bovine papillomavirus and a sequence relating to the replication thereof so that it is replicated in the absence of incorporation into a chromosome and episomally present. Examples thereof include containing EBNA-1 and oriP or Large T and SV40ori sequences (WO 2009/115295, WO 2009/157201, and WO 2009/149233). An expression vector for polycistronic expression may be used to simultaneously introduce a plurality of nuclear reprogramming substances. For polycistronic expression, gene-encoding sequences may be bound to each other through IRES or foot and mouth disease virus (FMDV) 2A coding region (Science, 322: 949-953, 2008; and WO 2009/092042 and WO 2009/152529).

To increase the efficiency of the induction of iPS cells in nuclear reprogramming, in addition to the above factors, for example, a histone deacetylase (HDAC) inhibitor [e.g., a small molecule inhibitor such as valproic acid (VPA) (Nat. Biotechnol., 26(7): 795-797 (2008)), trichostatin A, sodium butyrate, MC1293, or M344, or a nucleic acid expression inhibitor such as siRNA or shRNA against HDAC (e.g., HDAC1 siRNA Smartpool (R) (Millipore)) or HuSH 29mer shRNA Constructs against HDAC1 (OriGene)], a DNA methyltransferase inhibitor (e.g., 5'-azacytidine) (Nat. Biotechnol., 26(7): 795-797 (2008)), a G9a histone methyltransferase inhibitor [e.g., a small molecular inhibitor such as BIX-01294 (Cell Stem Cell, 2: 525-528 (2008)) or a nucleic acid expression inhibitor such as siRNA or shRNA against G9a (e.g., G9a siRNA (human) (Santa Cruz Biotechnology))], a L-channel calcium agonist (e.g., Bayk8644) (Cell Stem Cell, 3, 568-574 (2008)), a p53 inhibitor (e.g., siRNA or shRNA against p53) (Cell Stem Cell, 3, 475-479 (2008)), a Wnt signaling activator (e.g., soluble Wnt3a) (Cell Stem Cell, 3, 132-135 (2008)), a growth factor such as LIF or bFGF, an ALK5 inhibitor (e.g., SB431542) (Nat. Methods, 6: 805-8 (2009)), a mitogen-activated protein kinase signaling inhibitor, a glycogen synthase kinase-3 inhibitor (PloS Biology, 6(10), 2237-2247 (2008)), and miRNA such as miR-291-3p, miR-294, or miR-295 (R. L. Judson et al., Nat. Biotech., 27:459-461 (2009)) can be used.

For the method involving increase of the endogenous expression of a protein as a nuclear reprogramming substance using an agent, examples of the agent include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2H)-benzothiazolyl)ethanone HBr (pifithrin-alpha), prostaglandin J2, and prostaglandin E2 (WO 2010/068955).

Culture media for inducing iPS cells include, for example, (1) DMEM, DMEM/F12, or DME medium containing 10 to 15% FBS (these media may further properly contain LIF, penicillin/streptomycin, puromycin, L-glutamine, nonessential amino acids, β-mercaptoethanol, and the like.) and (2) a medium for ES cell culture, containing bFGF or SCF, for example, a medium for mouse ES cell culture (e.g., TX-WES medium (Thrombo X)) or a medium for primate ES cell culture (e.g., a medium for primate (human and monkey) ES cells (ReproCell, Kyoto, Japan), mTeSR-1).

As an example of a culture method, somatic cells can be contacted with a nuclear reprogramming substance (DNA or protein) in 10% FBS-containing DMEM or DMEM/F12 medium at 37° C. in the presence of 5% $CO_2$ for culture for about 4 to 7 days, followed by reseeding the cells on feeder cells (for example, mitomycin C-treated STO cells or SNL cells), culturing the cells in a bFGF-containing medium for primate ES cell culture from about 10 days after the contact between the somatic cells and the nuclear reprogramming substance, and generating ES cell-like colonies about 30 to about 45 days or more after the contact. To increase the efficiency of the induction of iPS cells, culture may also be performed under conditions of an oxygen concentration as low as 5 to 10%.

Alternatively, as an alternative culture method therefor, culture can be performed in 10% FBS-containing DMEM medium (which may further properly contain LIF, penicillin/streptomycin, puromycin, L-glutamine, nonessential amino acids, β-mercaptoethanol, and the like.) on feeder cells (for example, mitomycin C-treated STO cells or SNL cells), followed by generating ES cell-like colonies about 25 to about 30 days or more thereafter.

During the above culture, the medium is replaced with a fresh medium once daily from the 2nd day after starting the culture. The number of the somatic cells used in nuclear programming is not limited; however, it is in the range of about $5 \times 10^3$ to about $5 \times 10^6$ per 100 $cm^2$ of culture dish.

When a gene containing a drug-resistant gene is used as a marker gene, marker gene-expressing cells can be selected by culture in a medium containing the corresponding drug (a selection medium). Marker gene-expressing cells can also be detected by observation under a fluorescence microscope when the marker gene is a fluorescent protein gene, by adding a light-emitting substrate when it is a luciferase gene, or by adding a chromogenic substrate when it is a chromogenic enzyme gene.

As used herein, "somatic cell" may be any cell other than a germ cell, derived from a mammal (for example, a human, a mouse, a monkey, a pig, or a rat); examples thereof include keratinized epithelial cells (e.g., keratinized epidermal cells), mucosal epithelial cells (e.g., epithelial cells of the tongue surface), exocrine gland epithelial cells (e.g., mammary gland cells), hormone-secreting cells (e.g., adrenomedullary cells), cells for metabolism/storage (e.g., liver cells), luminal epithelial cells forming the interface (e.g., type I alveolar cells), luminal epithelial cells of an inner chain tube (e.g., vascular endothelial cells), ciliated cells having transport capacity (e.g., tracheal epithelial cells), cells for extracellular matrix secretion (e.g., fibroblasts), constrictive cells (e.g., smooth muscle cells), cells of the blood and the immune system (e.g., T lymphocytes), sense-related cells (e.g., rod cells), autonomic neurons (e.g., cholinergic neurons), sustentacular cells of sensory organs and peripheral neurons (e.g., satellite cells), neurons and glia cells in the central nervous system (e.g., astroglia cells), pigment cells (e.g., retinal pigment epithelial cells), and progenitor cells (tissue progenitor cells) thereof. There is no particular limitation on the degree of cell differentiation, the age of an animal from which cells are collected, and the like; even undifferentiated progenitor cells (including somatic stem cells) or even finally differentiated mature cells can be similarly used as a source of the somatic cells according to the present invention. Here, examples of undifferentiated progenitor cells include tissue stem cells (somatic stem cells) such as neural stem cells, hematopoietic stem cells, mesenchymal stem cells, and dental pulp stem cells.

According to the present invention, the animal individual from which somatic cells are collected is not particularly limited; however, it is preferably a human. When iPS cells are used as a material for cells for implantation, it is desirable to use somatic cells whose HLA genotype is the same or substantially the same as that of an individual to be subjected to implantation in view of no occurrence of rejection. Here, "substantially the same" refers to the matching of HLA genotype to such an extent that immune reaction against implanted cells can be suppressed by an immunosuppressant agent; the somatic cells are, for example, somatic cells having an HLA type for which the three gene loci of HLA-A, HLA-B, and HLA-DR or the four gene loci resulting from adding HLA-C are matched.

<Method for Simultaneously Producing Cardiomyocyte, Endothelial Cell, and Mural Cell from Induced Pluripotent Stem Cell>

For the purpose of the present invention, the cardiomyocytes mean cells at least expressing cardiac troponin (cTnT) or αMHC. cTnT is exemplified by NCBI accession number NM_000364 in the case of humans and by NM_001130174 in the case of mice. αMHC is exemplified by NCBI accession number NM_002471 in the case of humans and by NM_001164171 in the case of mice.

For the purpose of the present invention, the endothelial cells mean cells expressing any one of PE-CAM, VE-cadherin, and von Willebrand factor (vWF). The mural cells mean cells expressing smooth muscle actin (SMA). Here, PE-CAM is exemplified by NCBI accession number NM_000442 in the case of humans and by NM_001032378 in the case of mice. VE-cadherin is exemplified by NCBI accession number NM_001795 in the case of humans and by NM_009868 in the case of mice. vWF is exemplified by NCBI accession number NM_000552 in the case of humans and by NM_011708 in the case of mice. SMA is exemplified by NCBI accession number NM_001141945 in the case of humans and by NM_007392 in the case of mice.

The present invention can simultaneously produce cardiomyocytes, endothelial cells, and mural cells from induced pluripotent stem cells by the steps of:

(a) producing cardiomyocytes from induced pluripotent stem cells, and (b) culturing the cardiomyocytes in the presence of VEGF.

Here, the method for producing cardiomyocytes from induced pluripotent stem cells may be, for example, a method which involves producing cardiomyocytes from pluripotent stem cells as reported by Laflamme M A et al. (Laflamme M A & Murry C E, Nature 2011, Review). In addition, without particular limitation, examples thereof include a method which involves causing induced pluripotent stem cells to form a cell mass (an embryoid body) by floating culture to produce cardiomyocytes, a method which involves producing cardiomyocytes in the presence of a substance suppressing BMP signaling (WO2005/033298), a method which involves adding Activin A and BMP in that order to produce cardiomyocytes (WO2007/002136), a method which involves producing cardiomyocytes in the presence of a substance promoting the activation of the canonical Wnt signaling pathway (WO2007/126077), and a method which involves isolating Flk/KDR-positive cells from induced pluripotent stem cells and producing cardiomyocytes in the presence of cyclosporin A (WO2009/118928).

The present invention may further comprise a step of removing undifferentiated cells from the mixed cells of cardiomyocytes, endothelial cells, and mural cells prepared in the above steps.

[Method for Producing Cardiomyocyte from Induced Pluripotent Stem Cell]

According to the present invention, a method is exemplified, which involves producing cardiomyocytes by the steps of:

(i) culturing induced pluripotent stem cells in a medium containing Activin A, and (ii) after the step (i), further culturing the cells in a medium containing BMP4 and bFGF.

(i) Step of Culture in Medium Containing Activin A

In this step, the induced pluripotent stem cells obtained as described above may be separated by any method and cultured by floating culture or subjected to adhesive culture using a coating-treated culture dish. Preferred is adhesive culture. Here, the separation method may be a mechanical method or a method using a separation solution having protease activity and collagenase activity (for example, Accutase™ and Accumax™) or a separation solution having only collagenase activity. Preferred is a method which involves dissociating the cells using the separation solution only having collagenase activity and finely separating them mechanically. Here, the induced pluripotent stem cells are preferably used in the form of colonies cultured until they become 80% confluent on the dish used.

Here, the floating culture refers to culturing cells in a state of nonadhesion to a culture dish and is not particularly limited; it can be performed using a culture dish not artificially treated for the purpose of improving adhesion to the cells (for example, not coating-treated with an extracellular matrix) or a culture dish treated to artificially suppress adhesion (for example, coating-treated with polyhydroxyethyl methacrylate (poly-HEMA)).

The adhesive culture is performed in any medium in a coating-treated culture dish. Examples of a coating agent include Matrigel (BD), collagen, gelatin, laminin, heparan sulfate proteoglycan, entactin, and a combination thereof. Preferred is Matrigel. Adhesive culture is more preferable which uses a Matrigel sandwich method involving coating the whole induced pluripotent stem cells with Matrigel by causing the induced pluripotent stem cells to adhere to a culture dish coating-treated with Matrigel and further adding Matrigel.

The medium in this step can be prepared using a medium used for the culture of animal cells as a basal medium. The basal medium encompasses, for example, IMDM medium, Medium 199 medium, Eagle's minimum essential medium (EMEM) medium, αMEM medium, Doulbecco's modified Eagle's medium (DMEM) medium, Ham's F12 medium, RPMI 1640 medium, Fischer's medium, and a mixed medium thereof. Preferred is RPMI 1640 medium. The medium may contain serum, or may be serum-free. If necessary, it may contain one or more serum substitutes such as albumin, transferrin, Knockout Serum Replacement (KSR) (a serum substitute of FBS in ES cell culture), N2 supplement (Invitrogen), B27 supplement (Invitrogen), fatty acid, insulin, collagen precursor, trace element, 2-mercaptoethanol, and 3'-thiolglycerol, or may contain one or more substances such as lipid, amino acid, L-glutamine, Glutamax (Invitrogen), nonessential amino acid, vitamin, growth factor, antibiotic, antioxidant, pyruvic acid, buffer, and inorganic salt. According to the present invention, preferred examples of the growth factor include Wnt1, Wnt3, Wnt3a, Wnt4, Wnt7a, TGF-β, Activin A, Nodal, BMP2, BMP4, BMP6, BMP7, GDF, bFGF, and VEGF. In this step, it is desirable to at least use Activin A (e.g., (recombinant) human Activin A) as a growth factor.

According to the present invention, preferred examples of the medium include RPMI medium containing L-glutamine, B27 supplement, and Activin A.

The concentration of Activin A added to the medium is, for example, but not limited to, 10 ng/mL, 25 ng/mL, 50 ng/mL, 60 ng/mL, 70 ng/mL, 80 ng/mL, 90 ng/mL, 100 ng/mL, 110 ng/mL, 120 ng/mL, 130 ng/mL, 140 ng/mL, 150 ng/mL, 175 ng/mL, or 200 ng/mL Preferably, the concentration of Activin A added to the medium is 100 ng/mL.

The culture temperature is, but not limited to, about 30 to 40° C., preferably about 37° C. Culture is performed in an atmosphere of $CO_2$-containing air; the concentration of $CO_2$ is preferably about 2 to 5%. The culture time is, for example, is 1 day to 5 days, preferably 1 day.

(ii) Step of Culture in Medium Containing BMP and bFGF

In this step, when the preceding step has been performed by floating culture, the resultant cell population may be directly cultured in any medium in a coating-treated culture dish. Examples of the coating agent include Matrigel (BD), collagen, gelatin, laminin, heparan sulfate proteoglycan, entactin, and a combination thereof. Preferred is Matrigel. Alternatively, when the preceding step has been performed by adhesive culture, culture may be continued by medium replacement.

The medium used in this step can be prepared using a medium used for the culture of animal cells as a basal medium. The basal medium encompasses, for example, IMDM medium, Medium 199 medium, Eagle's minimum essential medium (EMEM) medium, αMEM medium, Doulbecco's modified Eagle's medium (DMEM) medium, Ham's F12 medium, RPMI 1640 medium, Fischer's medium, and a mixed medium thereof. Preferred is RPMI 1640 medium. The medium preferably contains no serum. If necessary, it may contain one or more serum substitutes such as albumin, transferrin, sodium selenite, ITS-X (Invitrogen) (containing insulin, transferrin, and sodium selenite), Knockout Serum Replacement (KSR) (a serum substitute of FBS in ES cell culture), N2 supplement (Invitrogen), B27 supplement (Invitrogen), fatty acid, insulin, collagen precursor, trace element, 2-mercaptoethanol, and 3'-thiolglycerol, or may contain one or more substances such as lipid, amino acid, L-glutamine, Glutamax, nonessential amino acid, vitamin, growth factor, antibiotic, antioxidant, pyruvic acid, buffer, and inorganic salt. According to the present invention, preferred examples of the growth factor include Wnt1, Wnt3, Wnt3a, Wnt4, Wnt7a, TGF-β, Activin A, Nodal, BMP2, BMP4, BMP6, BMP7, GDF, bFGF, and VEGF. In this step, it is desirable to at least use BMP4 (e.g., (recombinant) human BMP4) and bFGF (e.g., (recombinant) human bFGF) as growth factors.

According to the present invention, preferred examples of the medium include RPMI medium containing L-glutamine, B27 supplement, BMP4, and bFGF.

The concentration of BMP4 added to the medium is, for example, but not limited to, 0.1 ng/mL, 0.5 ng/mL, 1 ng/mL, 2.5 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 17.5 ng/mL, 20 ng/mL, 30 ng/mL, 40 ng/mL, or 50 ng/mL. The concentration of BMP4 added to the medium is preferably 10 ng/mL.

The concentration of bFGF added to the medium is, for example, but not limited to, 0.1 ng/mL, 0.5 ng/mL, 1 ng/mL, 2.5 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 17.5 ng/mL, 20 ng/mL, 30 ng/mL, 40 ng/mL, or 50 ng/mL. The concentration of bFGF added to the medium is preferably 10 ng/mL.

The culture temperature is, but not limited to, about 30 to 40° C., preferably about 37° C. Culture is performed under an atmosphere of $CO_2$-containing air; the concentration of $CO_2$ is preferably about 2 to 5%. The culture time is, for example, is 1 day to 10 days, preferably 4 days.

[Method for Culturing Cardiomyocytes in the Presence of VEGF]

In this step, the cardiomyocytes obtained by the above-described method can be further cultured in the presence of VEGF to produce mixed cells having a desired constitution ratio of cardiomyocytes, endothelial cells, and mural cells.

For example, the obtained cardiomyocytes may be cultured in any medium in a coating-treated culture dish when a cell population is obtained after floating culture in the preceding step. Examples of the coating agent include Matrigel (BD), collagen, gelatin, laminin, heparan sulfate proteoglycan, entactin, and a combination thereof. Preferred is Matrigel. Alternatively, in this step, the cells obtained by adhesive culture in the above-described step may continue to be cultured by medium replacement.

The medium used in this step can be prepared using a medium used for the culture of animal cells as a basal medium. The basal medium encompasses, for example, IMDM medium, Medium 199 medium, Eagle's minimum essential medium (EMEM) medium, αMEM medium, Doulbecco's modified Eagle's medium (DMEM) medium, Ham's F12 medium, RPMI 1640 medium, Fischer's medium, and a mixed medium thereof. Preferred is RPMI 1640 medium. The medium preferably contains no serum. If necessary, it may contain one or more serum substitutes such as albumin, transferrin, sodium selenite, ITS-X (Invitrogen) (containing insulin, transferrin, and sodium selenite), Knockout Serum Replacement (KSR) (a serum substitute of FBS in ES cell culture), N2 supplement (Invitrogen), B27 supplement (Invitrogen), fatty acid, insulin, collagen precursor, trace element, 2-mercaptoethanol, and 3'-thiolglycerol, or may contain one or more substances such as lipid, amino acid, L-glutamine, Glutamax, nonessential amino acid, vitamin, growth factor, small molecular compound, antibiotic, antioxidant, pyruvic acid, buffer, and inorganic salt. According to the present invention, preferred examples of the growth factor include Wnt1, Wnt3, Wnt3a, Wnt4, Wnt7a, TGF-β, Activin A, Nodal, BMP2, BMP4, BMP6, BMP7, GDF, bFGF, and VEGF. In this step, it is desirable to at least use VEGF as a growth factor.

According to the present invention, preferred examples of the medium include RPMI 1640 medium containing L-glutamine, B27 supplement, and VEGF.

The concentration of VEGF added to the medium can be, for example, in the range of 10 ng/mL to 500 ng/mL, 25 ng/mL to 300 ng/mL, 40 ng/mL to 200 ng/mL, 50 ng/mL to 100 ng/mL, 60 ng/mL to 90 ng/mL, or 65 ng/mL to 85 ng/mL. The concentration of VEGF added to the medium is preferably 50 ng/mL to 100 ng/mL. The concentration of VEGF added to the medium may also be, but not limited to, 10 ng/mL, 25 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, 100 ng/mL, 110 ng/mL, 120 ng/mL, 130 ng/mL, 140 ng/mL, 150 ng/mL, or 200 ng/mL The concentration of VEGF added to the medium is preferably 75 ng/mL.

The culture temperature is, but not limited to, about 30 to 40° C., preferably about 37° C. Culture is performed under an atmosphere of $CO_2$-containing air; the concentration of $CO_2$ is preferably about 2 to 5%. The culture time is, for example, 4 days to 20 days (for example, 5 to 15 days), preferably 10 days.

The cellular composition ratio of the cardiomyocytes, endothelial cells, and mural cells prepared by this method is, but not limited to; 40 to 80% (cardiomyocytes), 1 to 20% (endothelial cells), and 1 to 40% (mural cells), and 0.1 to 10% (undifferentiated cells). At least about 3% of endothelial cells are preferably contained. For the composition ratio of cardiomyocytes, endothelial cells, and mural cells, mixed cells are exemplified which have a composition ratio of cardiomyocytes, endothelial cells, mural cells, and undifferentiated cells of 62.7%:7.9%:18.3%:2.7%, respectively. The cellular composition ratio of cardiomyocytes, endothelial cells, and mural cells according to the present invention can optionally vary depending on the VEGF concentration and various other culture conditions; it can optionally vary within a range enabling the maintenance of moderate strength in sheeting the cells.

[Step of Removing Undifferentiated Cell (TRA-1-60 Positive Cell)]

The present invention may further comprise a step of removing undifferentiated cells from the mixed cells of cardiomyocytes, endothelial cells, and mural cells prepared in the above-described step.

In this step, any method can be adopted which can separate cardiomyocytes, endothelial cells, and mural cells, and undifferentiated cells in the mixed cells. The separation of cardiomyocytes, endothelial cells, and mural cells, and undifferentiated cells may be performed by a method which involves taking off only undifferentiated cells from the mixed cells on the basis of an indicator of undifferentiated cells, or by a method which involves taking off cardiomyocytes, endothelial cells, and mural cells from the mixed cells on the basis of indicators of cardiomyocytes, endothelial cells, and mural cells. The former method is preferably used in this step.

The indicator of undifferentiated cells can be a gene or a protein specifically expressed in undifferentiated cells. The gene or protein is well known in the art (Cell., 2005 Sep. 23; 122(6): 947-56; Stem Cells., 2004; 22(1): 51-64, Mol. Biol. Cell., 2002 April; 13(4): 1274-81); non-limited examples thereof include Oct3/4, Nanog (both of which are transcription factors), SSEA-3, SSEA-4, TRA-1-60, and TRA-1-81 (all of which are cell surface antigens). In this step, the indicator is preferably a cell surface antigen, particularly preferably TRA-1-60.

The indicators of cardiomyocytes, endothelial cells, and mural cells are, for example, but not limited to, cardiac troponin-T (cTnT) (cardiomyocytes), VE-cadherin (endothelial cells), and PDGFRb (mural cells).

In this step, the removal of undifferentiated cells is performed using a method such as flow cytometry (FACS) or magnetic cell sorting (MACS) on the basis of the above indicator. Preferred is MACS.

In a preferable embodiment of the present invention, the step of removing undifferentiated cells from the mixed cells is performed by capturing undifferentiated cells using a TRA-1-60 antibody and removing the captured undifferentiated cells (TRA-1-60 positive cells) by an immunomagnetic method (MACS).

The mixed cells after the step of removing undifferentiated cells may consist only of cardiomyocytes, endothelial cells, and mural cells, or may comprise any cells in addition to cardiomyocytes, endothelial cells, and mural cells. It is also likely that any cells described above comprise undifferentiated cells.

<Method for Producing Myocardial Sheet>

For the purpose of the present invention, the myocardial sheet means a sheet-like cell aggregate composed of various cells forming the heart or blood vessel, in which cells are connected by cell-cell junction. Here, the various cells forming the heart or blood vessel are exemplified by the above-described cardiomyocytes, endothelial cells, and mural cells.

The preferable myocardial sheet according to the present invention self-beats, has an electrical connection and orientation between cells, and has a uniform change in the calcium ion concentration gradient in response to beat.

The myocardial sheet is produced at least by further culturing the mixed cells of cardiomyocytes, endothelial cells, and mural cells simultaneously prepared by the above-described method.

The above culture may use a culture tool coated with a temperature-responsive polymer obtained by polymerization of a (meth)acrylamide compound, an N-(or N,N-di) alkyl-substituted (meth)acrylamide derivative (JP Patent Publication (Kokai) No. 2010-255001), or a vinyl ether derivative, preferably a culture tool on which poly-N-isopropylacrylamide is fixed. This culture tool can also be purchased as UpCell from WAKO.

The culture tool used for the above culture may be further coating-treated with any coating agent. Examples of the coating agent include Matrigel (BD), collagen, gelatin, laminin, heparan sulfate proteoglycan, entactin, and a combination thereof. Preferred is gelatin.

The medium used in this step can be prepared using a medium used for the culture of animal cells as a basal medium. The basal medium encompasses, for example, IMDM medium, Medium 199 medium, Eagle's minimum essential medium (EMEM) medium, αMEM medium, Doulbecco's modified Eagle's medium (DMEM) medium, Ham's F12 medium, RPMI 1640 medium, Fischer's medium, and a mixed medium thereof. Preferred is αMEM medium or RPMI 1640 medium. The medium preferably contains serum; however, if necessary, it may be replaced, for example, by albumin, transferrin, sodium selenite, ITS-X (Invitrogen) (containing insulin, transferrin, and sodium selenite), Knockout Serum Replacement (KSR) (a serum substitute of FBS in ES cell culture), N2 supplement (Invitrogen), B27 supplement (Invitrogen), fatty acid, insulin, collagen precursor, or trace element. This medium may further contain one or more substances such as 2-mercaptoethanol, 3'-thiolglycerol, lipid, amino acid, L-glutamine, Glutamax, nonessential amino acid, vitamin, growth factor, small molecular compound, antibiotic, antioxidant, pyruvic acid, buffer, and inorganic salt. According to the present invention, preferred examples of the growth factor include Wnt1, Wnt3, Wnt3a, Wnt4, Wnt7a, TGF-β, Activin A, Nodal, BMP2, BMP4, BMP6, BMP7, GDF, bFGF, and VEGF. In this step, it is desirable to at least use VEGF as a growth factor. In addition, the small molecular compound is exemplified by a Rho kinase (ROCK) inhibitor.

The ROCK inhibitor is not particularly limited provided that it can suppress the function of Rho kinase (ROCK); examples thereof include Y-27632 (see, for example, Ishizaki et al., Mol. Pharmacol. 57, 976-983 (2000); Narumiya et al., Methods Enzymol. 325, 273-284 (2000)), Fasudil/HA1077 (see, for example, Uenata et al., Nature 389: 990-994 (1997)), H-1152 (see, for example, Sasaki et al., Pharmacol. Ther. 93: 225-232 (2002)), Wf-536 (see, for example, Nakajima et al., Cancer Chemother Pharmacol. 52(4): 319-324 (2003)), and derivatives thereof and an antisense nucleic acid and an RNA interference-inducing nucleic acid (for example, siRNA) against ROCK and a dominant negative variant thereof, and expression vectors thereof. Other small molecular compounds are also known as ROCK inhibitors; thus, these compounds or derivatives thereof can also be used in the present invention (see, for example, U.S. Patent Application Publication Nos. 20050209261, 20050192304, 20040014755, 20040002508, 20040002507, 20030125344, and 20030087919 and International Publication Nos. WO2003/062227, WO2003/059913, WO2003/062225, WO2002/076976, and WO2004/039796). In the present invention, ROCK inhibitors are used alone or in a combination of 2 or more thereof.

According to the present invention, preferred examples of the medium include αMEM medium containing serum, Y-27632, and VEGF or RPMI 1640 medium containing serum and VEGF.

In this step, the number of cells provided for culture can be properly changed according to the size of a desired sheet although it is, for example, $1 \times 10^4$ to $1 \times 10^8$; the size of the myocardial sheet can vary depending on the culture tool. The number of days in culture may be 1 to 10 days, preferably 4 days.

The cellular composition ratio of the cardiomyocytes, endothelial cells, and mural cells contained in the myocardial sheet simultaneously prepared by the above method may vary before and after the formation of the sheet; the composition ratio is, but not limited to, 30 to 70% for cardiomyocytes, 0.1 to 20% for endothelial cells, 1 to 40% for mural cells, and 0.1 to 10% for undifferentiated cells. For example, the composition ratio of cardiomyocytes, endothelial cells, and mural cells is 47.0% (cardiomyocytes), 4.1% (endothelial cells), 22.5% (mural cells), and 2.2% (undifferentiated cells).

In culture for producing the myocardial sheet, it is desirable to perform culture after removing undifferentiated cells retaining pluripotency for the purpose of preventing the formation of tumor after myocardial sheet implantation. The undifferentiated cells retaining pluripotency can be recognized, for example, by Nanog or Oct3/4.

The prepared myocardial sheet may be used following layering, and is preferably a three-layered myocardial sheet. In layering, myocardial sheets can be layered (preferably layered so that the myocardial sheets are slightly shifted from each other) in a culture solution, followed by jointing them by removing the culture solution. When a plurality of sheets are layered, the operation may be performed at a time and the operation is preferably performed for each layer.

<Treatment of Heart Disease>

The mixed cells and the myocardial sheet composed of cardiomyocytes, endothelial cells, and mural cells obtained by the above-described method can be used as a therapeutic agent for the heart diseases of animals (preferably humans). The therapeutic method for heart diseases may be directly administered to the cardiac muscle layer of the heart when it is mixed cells. At this time, cells may be administered alone, and can be preferably administered together with a scaffolding material as promoting engraftment. Here, the scaffolding material is exemplified by, but not limited to, a component of biological origin, such as collagen, or a synthetic polymer, such as polylactic acid, replacing that. The administration of the myocardial sheet can be achieved by disposing the sheet so as to cover a desired portion. Here, the "disposing the sheet so as to cover a desired portion" can be performed using a technique well known in the art. In disposition, it may be disposed in encompassing relation to tissue when the desired portion is large. To obtain a desired effect, administration can also be carried out by performing the disposition several times in the same portion. The disposition several times is desirably performed at time intervals sufficient for the engraftment of desired cells in tissue and the occurrence of vascularization. The mechanism of the treatment of heart diseases may be an effect resulting from the engraftment of the myocardial sheet, or an indirect action independent from the engraftment of the cells (for example, the effect of the recruitment of recipient-derived cells to a damaged area by the secretion of an attractant).

The myocardial sheet according to the present invention may comprise a cell scaffold material such as collagen, fibronectin, or laminin in addition to cardiomyocytes, endothelial cells, and mural cells. Alternatively, the myocardial sheet according to the present invention may comprise any type of cells (a plurality of types are also possible) other than cardiomyocytes, endothelial cells, and mural cells.

For the mixed cells or myocardial sheet used for the treatment of heart diseases, the mixed cells or myocardial sheet having any number of cells or any size, or any number of sheets may be used depending on the species of an animal having a disease of interest, the size of a disease treatment area, the method for treating a disease, and the like. Generally, with the increasing size of an animal species or an individual, the number of cells necessary for treatment is increased, the size of the myocardial sheet is enlarged, or the number of the sheets is increased.

Examples of the heart disease treated according to the present invention include, but not limited to, losses due to diseases or disorders, such as heart failure, ischemic heart disease, myocardial infarction, myocardiopathy, myocarditis, hypertrophic cardiomyopathy, dilated phase of hypertrophic cardiomyopathy, and dilated cardiomyopathy.

The present invention will be described below in further detail based on Examples. However, the scope of the invention is not to be limited to these Examples.

Example 1: Induction of Differentiation from Human iPS Cell to Cardiomyocyte, Endothelial Cell, and Mural Cell Human iPS cells (201B6) were obtained from Professor Yamanaka at Kyoto University and subjected to maintenance culture using the same method as the previously reported method (Uosaki H. et al. PLoS One 2011; 6: e23657). The details are as follows. Undifferentiated hiPS cells were seeded on a Falcon culture dish (10 cm) coated with Matrigel (growth factor reduced, 1:60 dilution, Invitrogen) and cultured and maintained using a medium in which 4 ng/mL of human bFGF (hbFGF, WAKO) was added to a conditioned medium (culture supernatant) (MEF-CM) from mouse embryonic fibroblasts (MEF). On this occasion, 10 ml of the medium was used in the 10 cm dish. The basal medium for the conditioned medium was prepared by mixing 471 mL of Knockout DMEM (GIBCO), 120 mL of Knockout serum replacement (KSR), 6 mL of NEAA, 3 mL of 200 mM L-glutamine, 55 mM 2-ME (mercaptoethanol) (GIBCO), and 4 ng/ml of hbFGF. The MEF used was one treated with Mitomycin-C(MMC) (WAKO) for 2.5 hours.

Cell colonies were detached every 4 to 6 days using CTK solution (0.1% collagenase IV, 0.25% trypsin, 20% KSR, and 1 mM $CaCl_2$ in phosphate buffered saline (PBS)), made in the form of a small clump using a cell strainer, and subcultured.

Subsequently, incubation was performed at 37° C. for 3 to 5 minutes using Versene (Invitrogen) to detach hiPS cells from the culture dish. After aspirating Versene, pipetting was carried out in MEF-CM for recovery in the form of single cells, followed by performing centrifugation and counting the number of cells. Then, 100,000 cells/$cm^2$ were seeded in a 6-well plate coated with Matrigel (Growth Factor Reduced Matrigel, BD Biosciences). The medium used was 4 ng/mL of hbFGF-containing MEF-CM (5 ml for the 6-well plate). Culture was carried out for 2 to 3 days without medium replacement, and medium replacement was performed with MEF-CM containing Matrigel (1:60 dilution) and 4 ng/mL hbFGF in the stage in which a confluent state was reached (Matrigel sandwich).

24 Hours later, to differentiation-induce cardiomyocytes, replacement was carried out with 100 ng/mL of an Actvin (ActA; R&D Systems)-containing RPMI+B27 medium (RPMI1640 (GIBCO), 2 mM L-glutamine, and ×1 B27 supplement without insulin (GIBCO)) (this day is defined as day 0 of differentiation induction). After 24 hours of culture, replacement was carried out with RPMI+B27 medium containing 10 ng/mL of human bone morphogenetic protein 4 (BMP4; R&D) and 10 ng/mL of hbFGF (day 1). After 4 days of culture, to further induce endothelial cells and mural cells, replacement was carried out with RPMI+B27 medium containing each of 3 concentrations (0, 50, and 100 ng/mL) of VEGF (rhVEGF, WAKO) (day 5). The medium was replaced with the same medium every 2 intervening days; after 10 days of culture, cells were recovered using AccuMax (Innovative Cell Technologies); and a portion thereof was used for FACS analysis (day 15).

The following antibodies were used for FACS analysis:
A) for cardiomyocytes, monoclonal antibodies for cardiac troponin-T (cTnT)(Neomarkers) (labeled with Alexa Fluor 488 using Zenon Mouse IgG Labeling Kits (Molecular Probes));
B) for endothelial cells, anti-human VE-cadherin-FITC (BD); and
C) for mural cells, anti-human PDGFRb-FITC (BD).

As a result, the cellular composition ratio was shown to be (1) 55.7% (cardiomyocytes (CM)), 0.4% (endothelial cells (EC)), 34.4% (mural cells (MC)) for 0 ng/ml VEGF, (2) 54.1% (CM), 13.4% (EC), 16.9% (MC) for 50 ng/ml VEGF, and (3) 35.7% (CM), 27.4% (EC), 18.0% (MC) for 100 ng/ml VEGF (FIG. 1).

Example 2: Preparation of Myocardial Sheet

The mixed cells (1,000,000 cells/well) of cardiomyocytes, endothelial cells, and mural cells prepared by the method of Example 1 was seeded on a temperature-sensitive culture dish (UpCell, WAKO) 12-multiwell plate coated with gelatin (Sigma-Aldrich) in 1 ml of aMEM+FBS medium (alpha minimum essential medium (αMEM) (GIBCO, Grand Island, N.Y.), 10% fetal bovine serum (FBS), and 5.5 mM 2-ME) to which 50 nM of VEGF (rhVEGF, WAKO) and 10 μM of Y-27632 (rock inhibitor, WAKO) were added, and cultured at 37° C. Two days after culture, the medium was replaced with RPMI+FBS medium (RPMI 1640, L-glutamine, and 10% FBS) containing 50 nM VEGF (rhVEGF, WAKO). After further 2 days of culture, UpCell was returned from 37° C. to room temperature to detach the cells in a sheet form to provide a myocardial sheet.

Example 3: Cellular Composition of Myocardial Sheet

The myocardial sheet prepared by the method of Example 2 was used to perform FACS analysis. The following antibodies were used for the analysis:
- A) for cardiomyocytes, monoclonal antibodies for cardiac troponin-T (cTnT)(Neomarkers) (labeled with Alexa Fluor 488 using Zenon Mouse IgG Labeling Kits (Molecular Probes));
- B) for endothelial cells, anti-human VE-cadherin-FITC (BD);
- C) for mural cells, anti-human PDGFRb-FITC (BD); and
- D) for undifferentiated cells, anti-human TRA1-60-FITC (BD).

Figure 2:
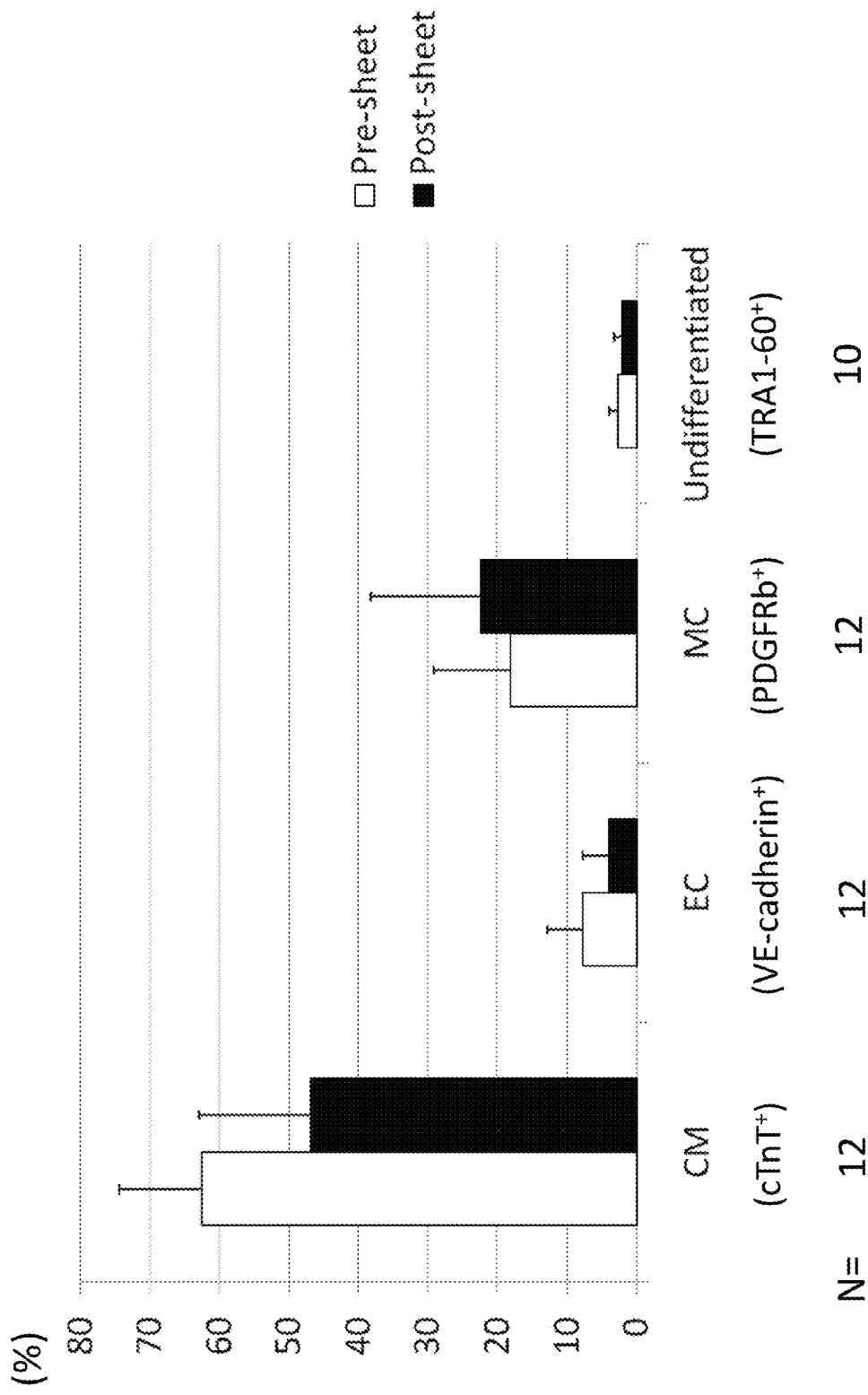
FIG. 2 is a graph showing the pre-sheet and post-sheet cellular composition ratios of cardiomyocytes (CM), endothelial cells (EC), mural cells (MC), and undifferentiated cells (Undifferentiated). In the figure, N indicates the number of samples.

Pre-sheet cells (cells immediately before seeding on UpCell) and post-sheet cells (cells immediately after recovering the myocardial sheet prepared through the step of preparing a myocardial sheet for 4 days) were used and subjected to FACS analysis. As a result, it was shown that the pre-sheet cellular composition ratio was 62.7±11.7% (CM), 7.9±4.9% (EC), 18.3±11.0% (MC), 2.7±1.3% (undifferentiated cells), while the post-sheet ratio was 47.0±15.9% (CM), 4.1±3.7% (EC), 22.5±15.7% (MC), 2.2±1.1% (undifferentiated cells) (FIG. 2).

Example 4: Electrophysiological Evaluation of Myocardial Sheet

For electrophysiological evaluation, the myocardial sheet prepared by the above method was allowed to dwell on the electrodes of a culture dish with electrodes, coated with 0.1% gelatin (MED64 system, Alpha Med Science). Subsequently, the medium was aspirated to fix the electrodes and the sheet, followed by slowly adding the medium and continuing culture. Two days later, the electric potential of each electrode was measured to record the conduction of the potential on the sheet. The results are shown in FIG. 3. Extracellular potential measurement confirmed that the beat was electrically continuous and was unidirectionally conducted. No site generating abnormal potential which was irregular, did not synchronize with the surroundings, and could be a trigger for arrhythmia was observed.

Example 5: Evaluation of Myocardial Sheet Based on Change in Calcium Concentration For evaluation based on a change in the calcium concentration, the myocardial sheet was fixed on a FALCON culture dish by the same method as in Example 4, followed by continuing culture. Two days after culture, the medium was replaced with a medium in which Fluo8 (Nacalai Tesque) was dissolved to a final concentration of 5 µM. After incubation at 37° C. for 1 hour, washing was performed two times with PBS, and the medium containing no Fluo8 was put therein. When fluorescence was detected using BZ-9000 (Keyence) to measure a change in the calcium concentration, a uniform change in the concentration gradient was observed along self-beat (FIG. 4).

Example 6: Layering of Myocardial Sheet

Figure 5:
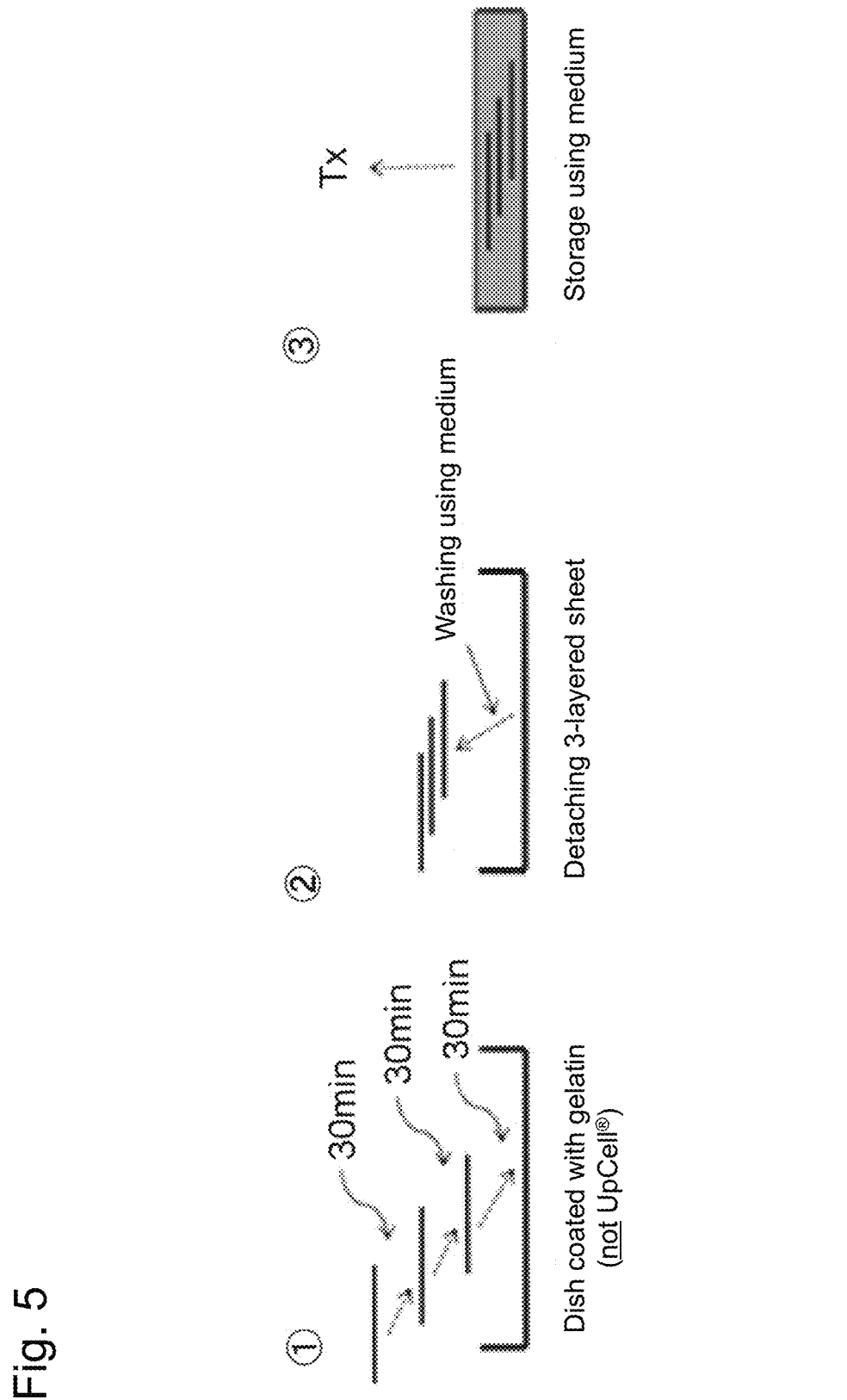
FIG. 5 is a schematic of a method for layering the cell sheet.

The myocardial sheet prepared by the methods of Examples 1 and 2 was spread and allowed to dwell on a dish coated with gelatin, and the medium was aspirated to fix the culture dish and the sheet, followed by medium addition and incubation at 37° C. for 30 minutes. Another myocardial sheet was spread and allowed to dwell on the sheet fixed on the dish, and the medium was aspirated for layering. The same step was repeated for 3 layers, and the 2nd and 3rd layers were layered so that each sheet was slightly shifted from original sheet. Thereafter, a Pipetman was used to flow a medium in such a manner that it ran along the bottom face of the culture dish, and the layered cell sheet was stripped off from the culture dish (FIGS. 5 and 6).

Example 7: Myocardial Sheet Implantation in Disease Model Rat and Cardiac Function Evaluation A sub-acute myocardial infarction (MI) model was prepared from 10 to 13-week old athymic immunodeficient rats (F344/N Jcl-rnu/rnu) weighing 250 to 330 g (Clea Japan, Inc.) by the following method. The rats were subjected to respiratory management with an artificial respirator for rats and anesthetized by isoflurane aspilation. Subsequently, the heart was exposed by pericardiotomy via left intercostal thoracotomy under artificial respiration using a small amount of oxygen, followed by ligating the anterior descending branch at the periphery of the first septal branch using a 6-0 polypropylene yarn. After confirming the reduced contraction and changed color tone of the periphery perfusion region (again administering the ligation when they were not observed), the surgical region was closed using a 4-0 polypropylene yarn. Six days later, the presence or absence of MI was confirmed by cardiac ultrasonography (Vivid7, GE Yokogawa Medical). A model having a left ventricular fractional shortening (FS) of more than 40% was excluded as an inappropriate model. Day 7 after MI introduction in this manner, the 3 myocardial sheets prepared by the above method were used by layering. For implantation, MI model rats were induced to anesthesia with diethyl ether and subjected to respiration management using an artificial respirator for rats, and the anesthesia was maintained with isoflurane. The thorax was opened by left intercostal thoracotomy, and the lung and the thoracic wall adhering to each other were cautiously detached to expose a myocardial infarction site, and the layered myocardial sheet was implanted on the infarction site. After allowing to dwell for 15 minutes, the surgical region was closed using a 4-0 polypropylene yarn. A myocardial infarction site was similarly exposed in a Sham surgery group, and the surgical region was similarly closed 15 minutes later.

Cardiac function was measured by cardiac ultrasonography 4 weeks and 3 months after implantation. The treatment group and the Sham group were evaluated for comparison (4 weeks after implantation: n=20 (treatment group)/18 (Sham group), 3 months after implantation: n=11 (treatment group)/8 (Sham group)).

Figure 7:
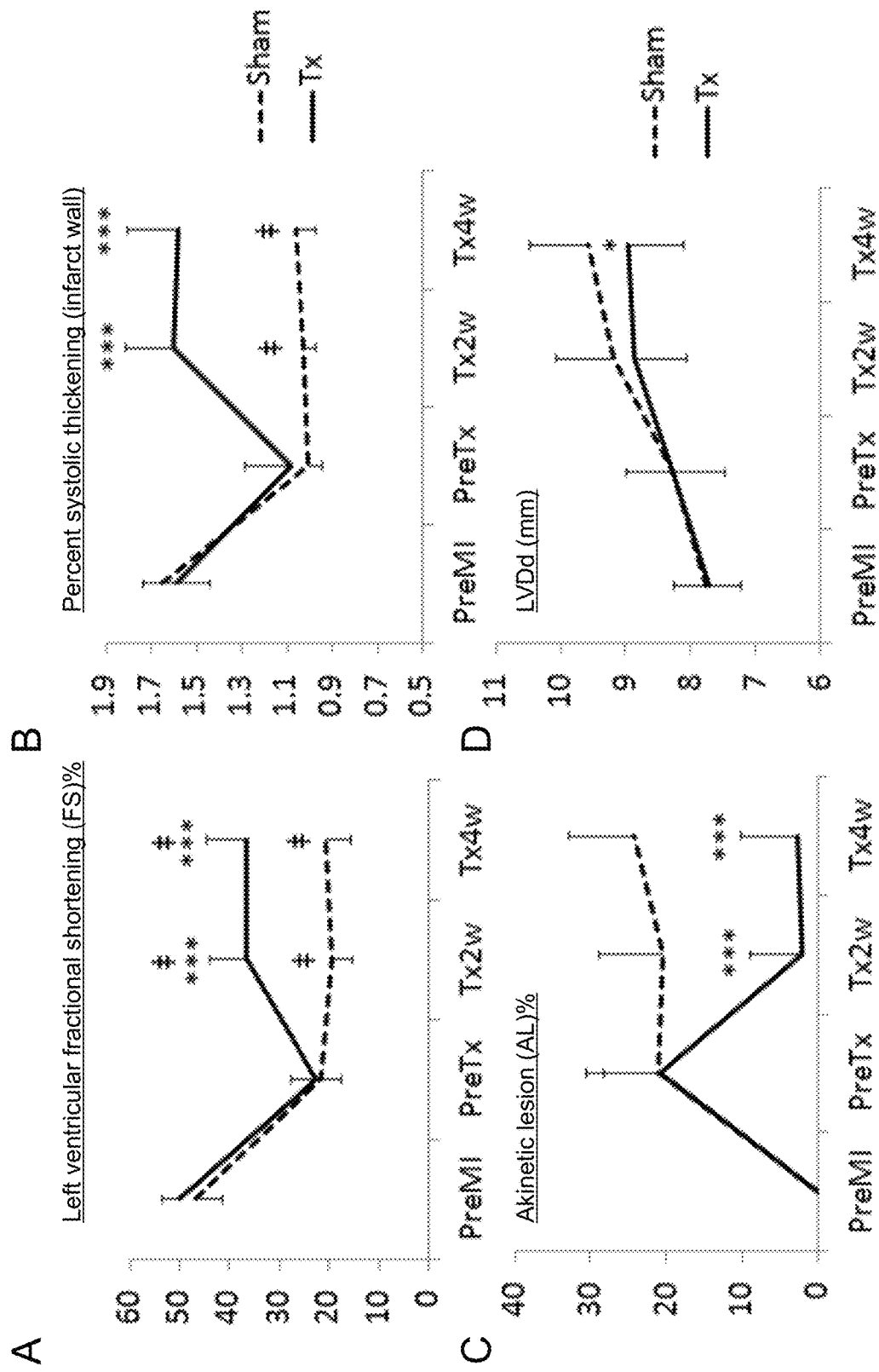
FIG. 7 is a series of graphs showing the results of cardiac ultrasonography up to 4 weeks after implantation. A and B are graphs showing changes in the left ventricular fractional shortening (FS) and the percent systolic thickening (both of which are indexes of contractile capacity) with time, respectively. C is a graph showing a change in the akinetic lesion (AL) (an index of the infarction range) with time. D is a graph showing a change in left ventricular diameter during diastole (LVDd) (an index of cardiac dilatation). In the figure, PreMI indicates before myocardial infarction; PreTx, before treatment; Tx2w, 2 weeks after treatment; and Tx4w, 4 weeks after treatment. * $p<0.05$,  $p<0.01$, * $p<0.001$ vs Sham/‡$p<0.001$ vs PreMI.
Figure 9:
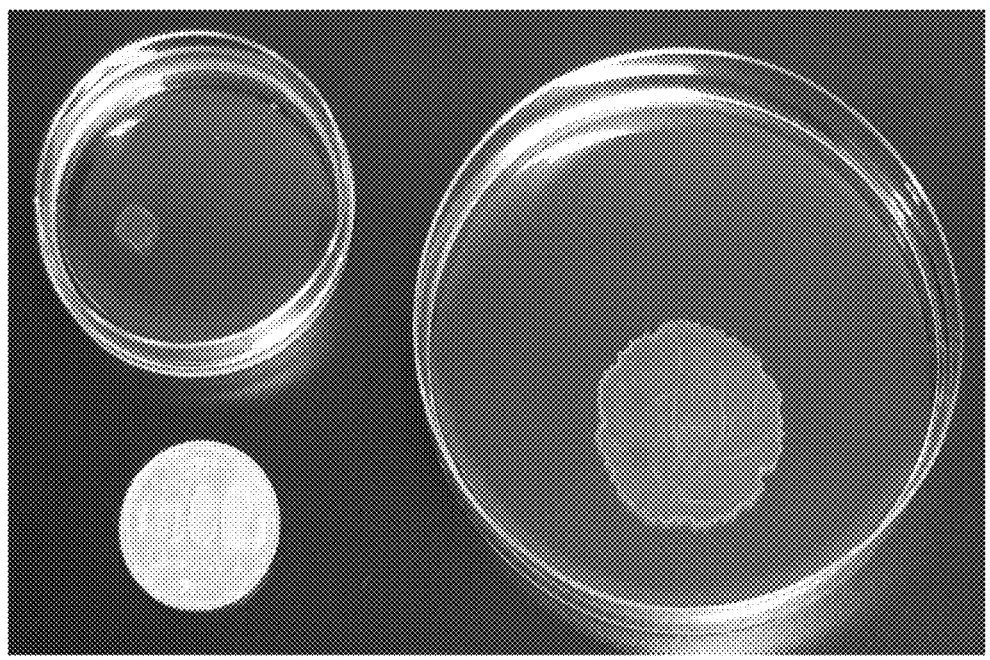
FIG. 9 is a photograph showing a macroscopic finding of an upsized myocardial sheet. The upper left shows a myocardial sheet for implantation in rats prepared in a 12-well; the right, the upsized myocardial sheet; and the lower left, a 500-yen coin. The upsized myocardial sheet had a diameter of about 34 mm.

The cardiac ultrasonography was carried out by the following method. The rats were induced to anesthesia with diethyl ether and subjected to respiration management using an artificial respirator for rats, and the anesthesia was maintained at such a depth to provide an RR interval of 120 to 200 msec with isoflurane. Subsequently, measurement was performed using a 10S probe (4.0 to 11.0 MHz). The septum diameter, left ventricular cavity diameter, and posterior wall diameter during diastole and systole were measured in M-mode to calculate the left ventricular fractional shortening (FS) and the percent systolic thickening. The left ventricular cavity area and left ventricular perimeter during diastole and systole were measured in B-mode to calculate the left ventricular fractional area change (FAC) and akinetic lesion (AL). During measurement, artificial respiration was stopped to remove bias due to respiration. As a result, FS, FAC, and systolic thickening indicating left ventricular systolic performance were observed to be improved 4 weeks and 3 months after treatment compared to those before treatment in the treatment group, and were shown to show significantly high values compared to those in the Sham group. The infarct size indicated by AL was also decreased at 4 weeks and 3 months thereafter compared to that before treatment and significantly limited compared to that in the Sham group. For the left ventricular diameter during diastole, a significant enlargement of the left ventricle was observed at the stage of 4 weeks in the Sham group compared to in the treatment group (FIGS. 7 and 8).

Example 8: Preparation of Large-Size Sheet

The mixed cells (8,000,000 to Ser. No. 10/000,000 cells/well) of cardiomyocytes, endothelial cells, and mural cells prepared by the method of Example 1 was seeded on a temperature-sensitive culture dish (10 cm UpCell dish, WAKO) coated with gelatin (Sigma-Aldrich) in 17 ml of aMEM+FBS medium (alpha minimum essential medium (αMEM) (GIBCO, Grand Island, N.Y.), 10% fetal bovine serum (FBS), and 5.5 mM 2-ME) to which 50 nM of VEGF (rhVEGF, WAKO) and 10 μM of Y-27632 (rock inhibitor, WAKO) were added and cultured at 37° C. Two days after culture, the medium was replaced with RPMI1640+L-glutamine+10% FBS medium containing 50 nM VEGF (rhVEGF, WAKO). After further 2 days of culture, UpCell was returned from 37° C. to room temperature to detach the cells in a sheet form to provide a large-size myocardial sheet.

Example 9: Removal of TRA-1-60 Positive Cell from Mixed Cells

The mixed cells of cardiomyocytes, endothelial cells, and mural cells at day 15 obtained by the method of Example 1 were recovered using AccuMax (Innovative Cell Technologies). An anti-human TRA-1-60-FITC antibody (BD) was added to the recovered cells, which was then incubated at room temperature for 20 minutes. Subsequently, anti-FITC MACS beads (Miltenyi) were added thereto, which was then incubated at 4° C. for 20 minutes. After washing, using autoMACS (Miltenyi), TRA-1-60 positive cells were immunomagnetically removed in dep1025-mode. The rate of recovery of TRA-1-60 negative cells is shown in Table 1.

TABLE 1

| | Total Number of Cells ($\times 10^4$) | Number of Negative Cells ($\times 10^4$) |
|---|---|---|
| 1 | 1000 | 199 (19.9%) |
| 2 | 2140 | 350 (16.4%) |
| 3 | 2000 | 526 (26.3%) |
| 4 | 2000 | 584 (29.2%) |
| 5 | 1840 | 518 (28.2%) |
| 6 | 3500 | 1096 (31.3%) |

Example 10: Preparation of Myocardial Sheet

The mixed cells (1,000,000 cells/well) after removing TRA-1-60 positive cells, prepared by the method of Example 9 were used to prepare a myocardial sheet by the same method as that of Example 2.

Figure 10:
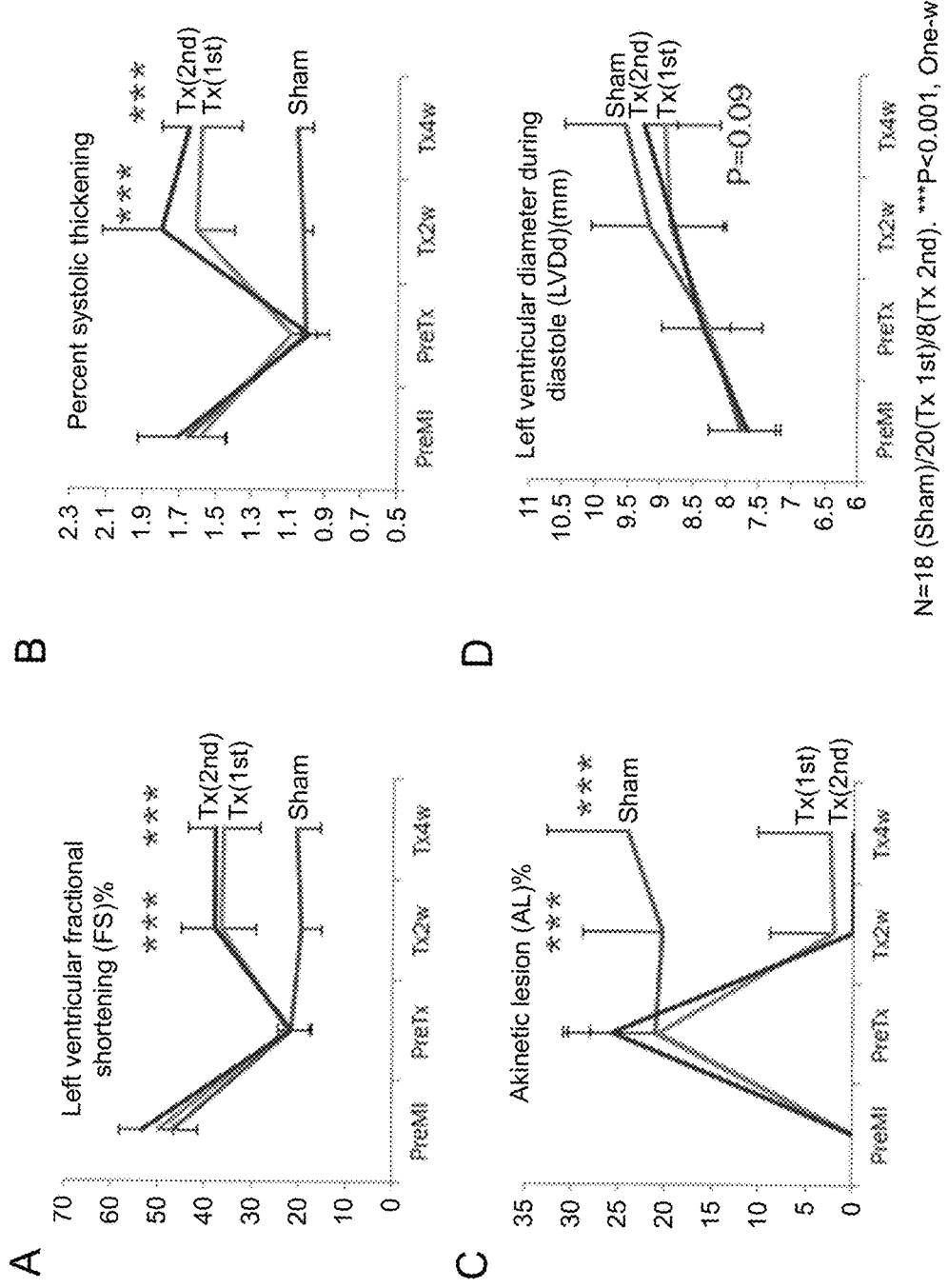
FIG. 10 is a series of graphs showing the results of cardiac ultrasonography after implanting cells excluding TRA1-60 positive cells in rats. A shows left ventricular fractional shortening (FS); B, percent systolic thickening (both of which are indexes of contractile capacity); C, the akinetic lesion (AL) (an index of the infarction range); and D, left ventricular diameter during diastole (LVDd) (an index of cardiac dilatation). In the figure, Tx(1st) indicates treatment using a first generation sheet (a sheet prepared by a method not comprising a step of removing TRA-1-60 positive cells), and Tx(2nd) indicates treatment using a second generation sheet (a sheet prepared by a method comprising a step of removing TRA-1-60 positive cells).

Example 11: Myocardial Sheet Implantation and Cardiac Function Evaluation in Disease Model Rat By the same method as that of Example 7, cardiac function was evaluated after implanting the myocardial sheet prepared by the method of Example 10 in disease model rats. The cardiac function was evaluated for the left ventricular fractional shortening (FS), the percent systolic thickening, the akinetic lesion (AL), and the left ventricular diameter during diastole (LVDd). The results are shown in FIG. 10.

As a result, the myocardial sheet prepared by the method of Example 10 caused the recovery of cardiac function 2 weeks after implantation to the disease model rats and the effect was also observed for 4 weeks thereafter. The formation of tumor was not seen in the observation until the 4 weeks thereafter.

INDUSTRIAL APPLICABILITY

The myocardial sheet of the present invention can be implanted on the heart disease affected area of a patient to cause the proliferation of normal cardiomyocytes as well as to promote vascularization with blood flow. This proves the use of the myocardial sheet of the present invention for regenerative medicine for treating heart diseases such as heart failure, ischemic heart disease, myocardial infarction, myocardiopathy, myocarditis, hypertrophic cardiomyopathy, dilated phase of hypertrophic cardiomyopathy, and dilated cardiomyopathy. The myocardial sheet of the present invention can also be used as a cardiac cell/tissue model for drug safety testing and drug discovery screening.

All publications, patents, and patent applications cited in this specification are intended to be incorporated herein by reference in their entirety.

The invention claimed is:

1. A myocardial sheet comprising cells derived from human induced pluripotent stem (iPS) cells, wherein a composition ratio of said cells derived from human iPS cells is 30 to 70% for cardiomyocytes, 0.1 to 20% for endothelial cells, and 1 to 40% for mural cells.

2. The myocardial sheet according to claim 1, wherein a composition ratio of TRA-1-60-positive undifferentiated cells in the cells derived from human iPS cells is 10% or less.

3. The myocardial sheet according to claim 1, wherein a composition ratio of TRA-1-60-positive undifferentiated cells in the cells derived from human iPS cells is 2.2% or less.

4. The myocardial sheet according to claim 1, wherein a composition ratio of TRA-1-60-positive undifferentiated cells in the cells derived from human iPS cells is 0.1% or more.

5. A layered myocardial sheet which comprises a plurality of myocardial sheets according to claim 1.

6. A method of treating heart disease comprising implanting the myocardial sheet according to claim 1 on the heart disease affected area of a patient suffering from heart disease.

7. A method of treating heart disease comprising implanting the layered myocardial sheet according to claim 5 on the heart disease affected area of a patient suffering from heart disease.

8. A mixed cell composition derived from human iPS cells which includes 40 to 80% of cardiomyocytes, 1 to 20% of endothelial cells and 1 to 40% of mural cells.

9. The mixed cell composition according to claim 8, wherein a composition ratio of TRA-1-60-positive undifferentiated cells is 10% or less.

10. The mixed cell composition according to claim 8, wherein a composition ratio of TRA-1-60-positive undifferentiated cells is 2.7% or less.

11. The mixed cell composition according to claim 8, wherein a composition ratio of TRA-1-60-positive undifferentiated cells is 0.1% or more.

12. A method for producing the myocardial sheet according to claim 1 comprising the steps of:
   culturing mixed cells including 40 to 80% of cardiomyocytes, 1 to 20% of endothelial cells and 1 to 40% of mural cells which are derived from human induced pluripotent stem cells using a culture tool coated with a temperature-responsive polymer, and
   recovering the myocardial sheet.

* * * * *